(12) United States Patent
Masuda et al.

(10) Patent No.: US 10,414,758 B2
(45) Date of Patent: *Sep. 17, 2019

(54) COMPOUNDS AND METHOD FOR TREATING AUTOIMMUNE DISEASES

(71) Applicant: Rigel Pharmaceuticals, Inc., South San Francisco, CA (US)

(72) Inventors: Esteban Masuda, Menlo Park, CA (US); Rajinder Singh, Belmont, CA (US); Vanessa Taylor, San Francisco, CA (US); Donald G. Payan, Hillsborough, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/875,897

(22) Filed: Jan. 19, 2018

(65) Prior Publication Data

US 2018/0141938 A1 May 24, 2018

Related U.S. Application Data

(63) Continuation of application No. 14/750,794, filed on Jun. 25, 2015, now Pat. No. 9,890,144, which is a continuation of application No. 14/163,822, filed on Jan. 24, 2014, now abandoned.

(60) Provisional application No. 61/756,781, filed on Jan. 25, 2013.

(51) Int. Cl.
| | |
|---|---|
| *A61K 31/506* | (2006.01) |
| *A61K 31/675* | (2006.01) |
| *C07D 413/12* | (2006.01) |
| *C07F 9/653* | (2006.01) |
| *A61K 45/06* | (2006.01) |

(52) U.S. Cl.
CPC .......... *C07D 413/12* (2013.01); *A61K 31/506* (2013.01); *A61K 31/675* (2013.01); *A61K 45/06* (2013.01); *C07F 9/65324* (2013.01); *Y10T 436/141111* (2015.01)

(58) Field of Classification Search
None
See application file for complete search history.

(56) References Cited

U.S. PATENT DOCUMENTS

| | | |
|---|---|---|
| 8,735,400 B2 | 5/2014 | Yan et al. |
| 2010/0190770 A1 | 7/2010 | Li et al. |
| 2010/0249092 A1 | 9/2010 | Singh et al. |
| 2014/0065153 A1 | 3/2014 | Christiano |

FOREIGN PATENT DOCUMENTS

| | | |
|---|---|---|
| WO | WO 2010/093808 | 8/2010 |
| WO | WO 2012/015972 | 2/2012 |

OTHER PUBLICATIONS

Gilhar et al., "Autoimmune Hair Loss (Alopecia Areata) Transferred by T Lymphocytes to Human Scalp Explants on SCID Mice," *The Journal of Clinical Investigation* 101(1):62-67, Jan. 1998.
Goodsaid et al., "Biomarker Qualification Pilot Process at the US Food and Drug Administration," *The AAPS Journal* 9(1):E105-E108, 2007.
"Guidance for Industry: Exposure-Response Relationships—Study Design, Data Analysis, and Regulatory Applications" (referred to as "Guidance") by U.S. Department of Health and Human Services; Food and Drug Administration; Center for Drug Evaluation and Research (CDER); Center for Biologics Evaluation and Research (CBER); published in Apr. 2003.
Pesu et al., "Jak3, Severe Combined Immunodeficiency, and a New Class of Immunosuppressive Drugs," *Immunological Reviews* 203(1):127-142, Feb. 1, 2005.
Sandborn et al., "Tofacitinib, an Oral Janus Kinase Inhibitor, in Active Ulcerative Colitis," *The New England Journal of Medicine* 367:616-624, Aug. 16, 2012.
International Search Report and Written Opinion, dated Mar. 19, 2014, from corresponding International Application No. PCT/US2014/012983.
Jabbari et al., "Targeting of JAK3 prevents onset of murine alopecia areata," *Journal of Investigative Dermatology*, Abstracts—Immunology 1: Adaptive Immunity, No. 610, 131:S104, 2012.
Price, "Therapy of alopecia areata: on the cusp and in the future," *Journal of Investigative Dermatology Symposium Proceedings*, vol. 8, No. 2: 207-211, 2003.

*Primary Examiner* — Jeffrey S Lundgren
*Assistant Examiner* — Michael J Schmitt
(74) *Attorney, Agent, or Firm* — Travis Young; Klarquist Sparkman, LLP

(57) ABSTRACT

Compounds and embodiments of a method for treating and/or preventing autoimmune diseases are disclosed. The method includes administering to a subject having an autoimmune disease, such as an inflammatory bowel disease, a therapeutically effective amount of a compound according to formula I

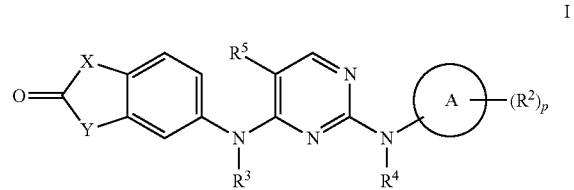

wherein X and Y independently are O or $NR^1$; each $R^1$ is independently H or $C_1$-$C_6$ alkyl; ring A is aryl; each $R^2$ independently is H, alkyl, alkoxy, amide, cyano, halo, haloalkyl, hydroxyalkyl, heteroalkyl, heterocyclyl, sulfonyl, sulfonamide, or two $R^2$ groups, taken together with the atom or atoms to which they are attached, combine to form a 4-10 membered ring system; p is 0, 1, 2, 3, or 4; $R^3$ and $R^4$ independently are H or $C_1$-$C_6$ alkyl; and $R^5$ is halo, cyano, or $C_1$-$C_6$ alkyl.

33 Claims, No Drawings

COMPOUNDS AND METHOD FOR TREATING AUTOIMMUNE DISEASES

CROSS REFERENCE TO RELATED APPLICATION

This application is a continuation of U.S. patent application Ser. No. 14/750,794, filed on Jun. 25, 2015, which is a continuation of Ser. No. 14/163,822, filed Jan. 24, 2014, which claims the benefit of U.S. Provisional Application No. 61/756,781, filed Jan. 25, 2013, all of which are incorporated herein in their entireties by reference.

FIELD

The present disclosure concerns pyrimidinediamine compounds and embodiments of a method for using the compounds to treat autoimmune diseases, such as inflammatory bowel diseases.

BACKGROUND

Inflammatory bowel diseases are a group of chronic inflammatory conditions that primarily affect the colon and small intestine. Inflammatory bowel diseases include, but are not limited to, Crohn's disease (also known as regional enteritis, Crohn's ileitis, and granulomatous colitis), collagenous colitis, granulomatous ileocolitis, idiopathic inflammatory bowel disease, ileitis, irritable bowel syndrome, lymphocytic colitis, regional enteritis, spastic colon, and ulcerative colitis. Common symptoms of inflammatory bowel diseases include intestinal inflammation (e.g., redness and/or swelling), abdominal pain, abdominal cramps, bloody diarrhea, vomiting, pelvic muscle spasms, and/or fever. Weight loss, sweats, malaise, and/or arthralgias also may occur. Inflammatory bowel disease symptoms typically wax and wane in intensity over time.

Two of the most common inflammatory bowel diseases are ulcerative colitis and Crohn's disease. Ulcerative colitis is characterized by inflammation that is primarily limited to the mucosa and submucosa of the colon, or large intestine, and the rectum. Crohn's disease can cause inflammation anywhere throughout the digestive tract, and penetrates deeper into the tissues.

In some cases, bowel inflammation results when the immune system attacks a pathogen, such as a virus or bacterium, or an intraluminal antigen, such as a protein from cow's milk. In other cases, inflammatory bowel disease may be an autoimmune process. Genetic predisposition also may have a role in certain cases.

Inflammatory bowel disease can severely impact a subject's life, and current therapies frequently provide unsatisfactory and insufficient relief.

SUMMARY

This disclosure concerns compounds and embodiments of a method for treating and/or preventing inflammatory bowel diseases. In some embodiments, a method for treating a disease, such as an inflammatory bowel disease includes administering to a subject identified as having an inflammatory bowel disease, or being at risk of developing an inflammatory bowel disease, a therapeutically effective amount of a compound according to formula I

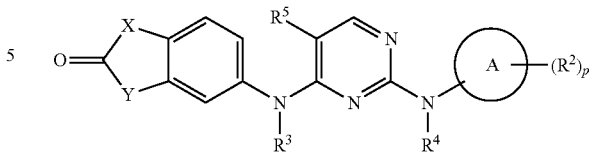

wherein X and Y independently are O or $NR^1$; each $R^1$ is independently H or $C_1$-$C_6$ alkyl; ring A is aryl; each $R^2$ independently is H, alkyl, alkoxy, amide, cyano, halo, haloalkyl, hydroxyalkyl, heteroalkyl, heterocyclyl, sulfonyl, sulfonamide, or two $R^2$ groups, taken together with the atom or atoms to which they are attached, combine to form a 4-10 membered ring system; p is 0, 1, 2, 3, or 4; $R^3$ and $R^4$ independently are H or $C_1$-$C_6$ alkyl; and $R^5$ is halo, cyano, or $C_1$-$C_6$ alkyl.

In some embodiments, ring A is phenyl. In certain embodiments, the compound has the formula

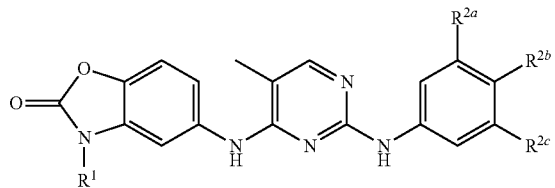

wherein $R^1$ is H or —$CH_2OP(O)(ONa)_2$, and $R^{2a}$-$R^{2c}$ are as defined above for $R^2$.

In particular embodiments, the compound is selected from the group consisting of N2-(3,4,5-trimethyl)phenyl-5-methyl-N4-(2-oxo-2,3-dihydro-1,3-benzoxazol-5-yl)-2,4-pyrimidinediamine; 4-[5-Methyl-4-(2-oxo-2,3-dihydro-benzooxazol-5-ylamino)-pyrimidin-2-ylamino]-N-phenyl-benzamide; N4-(benzo[d]oxazol-2(3H)-on-5-yl)-N2-(4-aminocarbonylphenyl)-5-methylpyrimidine-2,4-diamine; N2-(3,4-dimethyl-5-hydroxymethyl)phenyl-5-methyl-N4-(2-oxo-2,3-dihydro-1,3-benzoxazol-5-yl)-2,4-pyrimidinediamine; N-Cyclobutyl-4-[5-methyl-4-(2-oxo-2,3-dihydro-benzooxazol-5-ylamino)-pyrimidin-2-ylamino]-benzamide; N4-(benzo[d]oxazol-2(3H)-on-5-yl)-N2-(3-methylsulfonyl)phenyl)-5-methylpyrimidine-2,4-diamine; 5-(2-(3-(fluoromethyl)-5-methylphenylamino)-5-methylpyrimidin-4-ylamino)benzo[d]oxazol-2(3H)-one; N2-(3-fluoro-4-methyl)phenyl-5-methyl-N4-(2-oxo-2,3-dihydro-1,3-benzoxazol-5-yl)-2,4-pyrimidinediamine; N2-(3,5-dimethyl-4-hydroxymethyl)phenyl-5-methyl-N4-(2-oxo-2,3-dihydro-1,3-benzoxazol-5-yl)-2,4-pyrimidinediamine; 5-[2-(3,4-Dimethyl-phenylamino)-5-methyl-pyrimidin-4-ylamino]-3H-benzooxazol-2-one; 5-(2-(3-chloro-4,5-dimethoxyphenylamino)-5-methylpyrimidin-4-ylamino)benzo[d]oxazol-2(3H)-one; 5-(2-(benzo[d]isoxazol-6-ylamino)-5-methylpyrimidin-4-ylamino)benzo[d]oxazol-2(3H)-one; N2-(3-methoxy-5-trifluoromethyl)phenyl-5-methyl-N4-(2-oxo-2,3-dihydro-1,3-benzoxazol-5-yl)-2,4-pyrimidinediamine; N2-(3,5-dimethyl-4-fluoro)phenyl-5-methyl-N4-(2-oxo-2,3-dihydro-1,3-benzoxazol-5-yl)-2,4-pyrimidinediamine; N2-(3-methoxy-5-trifluoromethyl)phenyl-5-methyl-N4-[3-(phosphonooxy)methyl-2-oxo-2,3-dihydro-1,3-benzoxazol-5-yl]-2,4-pyrimidinediamine bis-sodium salt; sodium (5-(2-(4-fluoro-3-methoxy-5-methylphenylamino)-5-methylpyrimidin-4-ylamino)-2- oxobenzo[d]oxazol-3(2H)-yl)methyl phosphate; 5-methyl-N4-[3-(phosphonooxy)methyl-2-oxo-2,3-dihydro-1,3-benzoxazol-5-yl]-N2-(3,4,5-trimethyl)phenyl-2,4-pyrimidinediamine bis-sodium salt; and N2-(3,5-dimethyl-4-fluoro)phenyl-5-methyl-N4-[3-(phosphonooxy)methyl-2-oxo-2,3-dihydro-1,3-benzoxazol-5-yl]-2,4-pyrimidinediamine bis-sodium salt.

In some embodiments, the inflammatory bowel disease is Crohn's disease, collagenous colitis, granulomatous ileocolitis, idiopathic inflammatory bowel disease, ileitis, irritable bowel syndrome, lymphocytic colitis, regional enteritis, spastic colon, or ulcerative colitis.

Administering the compound may include exposing to the subject to a first dose of the compound or a pharmaceutical composition comprising the compound. In some embodiments, the method further includes determining a therapeutic blood level of the compound or a metabolite thereof in the subject. The method may further include comparing the therapeutic blood level to a control, and adjusting a second dose of the compound, based at least in part on the comparison, to optimize therapeutic effect. For example, if the therapeutic blood level is greater than a control, the second dose may be decreased relative to the first dose. Alternatively, if the therapeutic blood level is less than a control, the second dose may be increased relative to the first dose. In certain embodiments, the therapeutically effective dose is in the range of from about 0.0001 mg/kg body weight/day to about 100 mg/kg/day, such as from about 5 mg/kg body weight/day to about 20 mg/kg/day.

In one embodiment, the compound is administered serially in plural administrations to the subject. The method may include administering two or more compounds according to formula I serially or in combination to the subject. In some embodiments, the compound is administered as a pharmaceutical composition. The compound may be administered prophylactically.

In some embodiments, the method further includes administering a second therapeutic to the subject. The second therapeutic may be administered in combination with the compound, or prior to or subsequent to the compound. In some embodiments, the second therapeutic is an analgesic, an antibiotic, an anticoagulant, an antibody, an anti-inflammatory agent, an immunosuppressant, a guanylate cyclase-C agonist, an intestinal secretagogue, or a combination thereof. The anti-inflammatory agent may be a steroid or a non-steroidal anti-inflammatory agent. In certain embodiments, the nonsteroidal anti-inflammatory agent is selected from aminosalicylates, cyclooxygenase inhibitors, diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin, or a combination thereof. In some embodiments, the immunosuppressant is mercaptopurine, a corticosteroid, an alkylating agent, a calcineurin inhibitor, an inosine monophosphate dehydrogenase inhibitor, antilymphocyte globulin, antithymocyte globulin, an anti-T-cell antibody, or a combination thereof. In one embodiment, the antibody is infliximab.

Embodiments of a method for treating an inflammatory bowel disease include diagnosing a subject as being in need of treatment for an inflammatory bowel disease an inflammatory bowel disease, administering to the subject a therapeutically effective amount of one or more compounds disclosed herein, and evaluating the subject to determine a future course of treatment. In some embodiments, the therapeutic amount is a daily dose of from about 1 mg/day up to about 2 grams/day.

In one embodiment, a single compound is administered serially in plural administrations to the subject. In another embodiment, two or more compounds are administered either serially or in combination to the subject. In some embodiments, the one or more compounds are administered as a pharmaceutical composition. The pharmaceutical composition may include, in addition to the one or more compounds, an excipient, a second therapeutic, or both.

In some embodiments, the one or more compounds are administered parenterally, orally, or rectally. In certain embodiments, the one or more compounds are administered prophylactically.

Evaluating the subject to determine a future course of treatment may include determining a level of a biomarker associated with the inflammatory bowel disease. In some embodiments, the biomarker is a serologic biomarker, a genetic biomarker, a fecal biomarker, or a mucosal biomarker.

The foregoing and other objects, features, and advantages of the invention will become more apparent from the following detailed description, which proceeds with reference to the accompanying figures.

DETAILED DESCRIPTION

I. Terms and Abbreviations

Unless otherwise noted, technical terms are used according to conventional usage. As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all molecular weight or molecular mass values, given compounds are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

When chemical structures are depicted or described, unless explicitly stated otherwise, all carbons are assumed to include hydrogen so that each carbon conforms to a valence of four. For example, in the structure on the left-hand side of the schematic below there are nine hydrogen atoms implied. The nine hydrogen atoms are depicted in the right-hand structure.

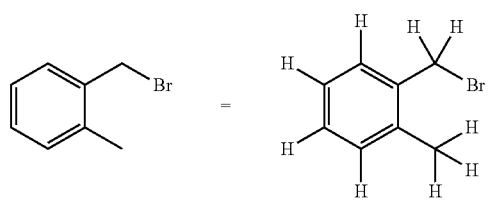

Sometimes a particular atom in a structure is described in textual formula as having a hydrogen or hydrogen atoms, for example —$CH_2CH_2$—. It will be understood by a person of ordinary skill in the art that the aforementioned descriptive techniques are common in the chemical arts to provide brevity and simplicity to description of organic structures.

In this application, some ring structures are depicted generically and will be described textually. For example, in the schematic below ring A may be used to describe a phenyl ring, a heteroaryl ring, such as a pyridine ring, and fused ring system. Again by way of example, if ring A is describes a phenyl ring, then there are four hydrogen atoms on ring A as well (when R is not H).

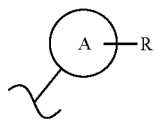

If a group R is depicted as "floating" on a ring system, as for example in the following structure

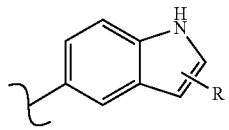

then, unless otherwise defined, R can reside on any atom of the bicyclic ring system, excluding the atom carrying the bond with the " ~ " symbol, so long as a stable structure is formed. In the example depicted, the R group can reside on any depicted carbon atom in either the 5-membered or the 6-membered ring of the indolyl ring system.

When there are more than one such depicted "floating" groups, as for example in the formulae

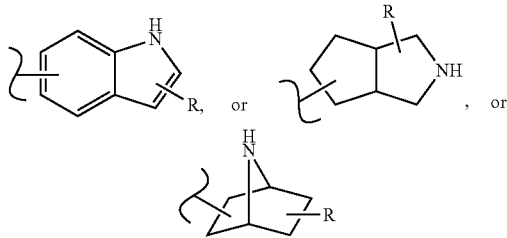

where there are two groups, namely, the R and the bond indicating attachment to a parent structure, then, unless otherwise defined, the "floating" groups can reside on any atoms of the ring system, again assuming each replaces a depicted, implied, or expressly defined hydrogen on the ring system and a chemically stable compound would be formed by such connectivity.

When a group R is depicted as existing on a ring system containing saturated carbons, as for example in the formula

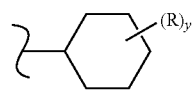

where, in this example, y can be more than one, assuming each replaces a currently depicted, implied, or expressly defined hydrogen on the ring, then, unless otherwise defined, two R's can reside on the same carbon. A simple example is when R is a methyl group, and the formula can depict geminal dimethyl groups bonded to a single carbon of the depicted ring (an "annular" carbon). In another example, two R's on the same carbon, including that same carbon, can form a ring, thus creating a spirocyclic ring (a "spirocyclyl" group) structure. Using the previous example, where two R's form, e.g. a piperidine ring in a spirocyclic arrangement with the cyclohexane, as for example in the formula

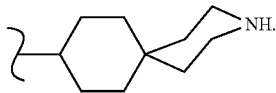

When a group with its bonding structure is denoted as being bonded to two partners; that is, a divalent radical, for example, —OCH$_2$—, then it is understood that either of the two partners can be bound to the particular group at one end, and the other partner is necessarily bound to the other end of the divalent group, unless stated explicitly otherwise. Stated another way, divalent radicals are not to be construed as limited to the depicted orientation, for example "—OCH$_2$—" is meant to mean not only "—OCH$_2$—" as drawn, but also "—CH$_2$O—."

"Alkyl" in its broadest sense is intended to include linear, branched, or cyclic hydrocarbon structures, and combinations thereof. Alkyl groups can be fully saturated or with one or more units of unsaturation, but not aromatic. Generally alkyl groups are defined by a subscript, either a fixed integer or a range of integers. For example, "C$_8$alkyl" includes n-octyl, iso-octyl, 3-octynyl, cyclohexenylethyl, cyclohexylethyl, and the like; where the subscript "8" designates that all groups defined by this term have a fixed carbon number of eight. In another example, the term "C$_{1-6}$alkyl" refers to alkyl groups having from one to six carbon atoms and, depending on any unsaturation, branches and/or rings, the requisite number of hydrogens. Examples of C$_{1-6}$alkyl groups include methyl, ethyl, vinyl, propyl, isopropyl, butyl, s-butyl, t-butyl, isobutyl, isobutenyl, pentyl, pentynyl, hexyl, cyclohexyl, hexenyl, and the like. When an alkyl residue having a specific number of carbons is named generically, all geometric isomers having that number of carbons are intended to be encompassed. For example, either "propyl" or "C$_3$alkyl" each include n-propyl, c-propyl, propenyl, propynyl, and isopropyl. Cycloalkyl is a subset of alkyl and includes cyclic hydrocarbon groups of from three to thirteen carbon atoms. Examples of cycloalkyl groups include c-propyl, c-butyl, c-pentyl, norbornyl, norbornenyl, c-hexenyl, adamantyl and the like. As mentioned, alkyl refers to alkanyl, alkenyl, and alkynyl residues (and combinations thereof)—it is intended to include, e.g., cyclohexylmethyl, vinyl, allyl, isoprenyl, and the like. An alkyl with a particular number of carbons can be named using a more specific but still generic geometrical constraint, e.g. "C$_{3-6}$cycloalkyl" which means only cycloalkyls having between 3 and 6 carbons are meant to be included in that particular definition. Unless specified otherwise, alkyl groups, whether alone or part of another group, e.g. —C(O)alkyl, have from one to twenty carbons, that is C$_{1-20}$alkyl. In the example "—C(O)alkyl," where there were no carbon count limitations defined, the carbonyl of the —C(O)alkyl group is not included in the carbon count, since "alkyl" is designated generically. But where a specific carbon limitation is given, e.g. in the term "optionally substituted C$_{1-20}$alkyl," where the optional substitution includes "oxo" the carbon of any carbonyls formed by such "oxo" substitution are included in the carbon count since they were part of the original carbon count limitation. However, again referring to "optionally substituted $C_{1-20}$alkyl," if optional substitution includes carbon-containing groups, e.g. —$CH_2CO_2H$, the two carbons in this group are not included in the $C_{1-20}$alkyl carbon limitation.

When a carbon number limit is given at the beginning of a term which itself comprises two terms, the carbon number limitation is understood as inclusive for both terms. For example, for the term "$C_{7-14}$arylalkyl," both the "aryl" and the "alkyl" portions of the term are included the carbon count, a maximum of 14 in this example, but additional substituent groups thereon are not included in the atom count unless they incorporate a carbon from the group's designated carbon count, as in the "oxo" example above. Likewise when an atom number limit is given, for example "6-14 membered heteroarylalkyl," both the "heteroaryl" and the "alkyl" portion are included the atom count limitation, but additional substituent groups thereon are not included in the atom count unless they incorporate a carbon from the group's designated carbon count. In another example, "$C_{4-10}$cycloalkylalkyl" means a cycloalkyl bonded to the parent structure via an alkylene, alkylidene or alkylidyne; in this example the group is limited to 10 carbons inclusive of the alkylene, alkylidene or alkylidyne subunit. As another example, the "alkyl" portion of, e.g. "$C_{7-14}$arylalkyl" is meant to include alkylene, alkylidene or alkylidyne, unless stated otherwise, e.g. as in the terms "$C_{7-14}$arylalkylene" or "$C_{6-10}$aryl-$CH_2CH_2$—."

"Alkoxy" refers to the group —O-alkyl, where alkyl is as defined herein. Alkoxy includes, by way of example, methoxy, ethoxy, n-propoxy, isopropoxy, n-butoxy, t-butoxy, sec-butoxy, n-pentoxy, cyclohexyloxy, cyclohexenyloxy, cyclopropylmethyloxy, and the like.

"Acyl" refers to the groups —C(O)H, —C(O)alkyl, —C(O)aryl and —C(O)heterocyclyl.

"Amide" refers to the group —C(O)$NH_2$ or —N(H)acyl.

"Amino" refers to the group —$NH_2$.

"Aryl" (sometimes referred to as "Ar") refers to a monovalent aromatic carbocyclic group of, unless specified otherwise, from 6 to 15 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, 9,10-dihydrophenanthrenyl, indanyl, tetralinyl, and fluorenyl and the like), provided that the point of attachment is through an atom of an aromatic portion of the aryl group and the aromatic portion at the point of attachment contains only carbons in the aromatic ring. If any aromatic ring portion contains a heteroatom, the group is a heteroaryl and not an aryl. Aryl groups are monocyclic, bicyclic, tricyclic or tetracyclic.

"Arylalkyl" refers to a residue in which an aryl moiety is attached to a parent structure via one of an alkylene, alkylidene, or alkylidyne radical. Examples include benzyl, phenethyl, phenylvinyl, phenylallyl and the like. When specified as "optionally substituted," both the aryl, and the corresponding alkylene, alkylidene, or alkylidyne portion of an arylalkyl group can be optionally substituted. By way of example, "$C_{7-11}$arylalkyl" refers to an arylalkyl limited to a total of eleven carbons, e.g., a phenylethyl, a phenylvinyl, a phenylpentyl and a naphthylmethyl are all examples of a "$C_{7-11}$arylalkyl" group.

"Arylene" refers to an aryl that has at least two groups attached thereto. For a more specific example, "phenylene" refers to a divalent phenyl ring radical. A phenylene, thus can have more than two groups attached, but is defined by a minimum of two non-hydrogen groups attached thereto.

"Aryloxy" refers to the group —O-aryl, where aryl is as defined herein, including, by way of example, phenoxy, naphthoxy, and the like.

"Autoimmune Disease" refers to those diseases which are commonly associated with the nonanaphylactic hypersensitivity reactions (Type II, Type III and/or Type IV hypersensitivity reactions) that generally result as a consequence of the subject's own humoral and/or cell-mediated immune response to one or more immunogenic substances of endogenous and/or exogenous origin. Such autoimmune diseases are distinguished from diseases associated with the anaphylactic (Type I or IgE-mediated) hypersensitivity reactions.

"Carboxyl," "carboxy" or "carboxylate" refers to —$CO_2H$ or salts thereof.

"Carboxyl ester" or "carboxy ester" or "ester" refers to the group —$CO_2$alkyl, —$CO_2$aryl or —$CO_2$heterocyclyl.

"Carbamate" refers to the group —OC(O)$NH_2$, —N(H)carboxyl or —N(H)carboxyl ester.

"Carbonate" refers to the group —$OCO_2$alkyl, —$OCO_2$aryl or —$OCO_2$heterocyclyl.

"Cyano" or "nitrile" refers to the group —CN.

"Halo" or "halogen" refers to fluoro, chloro, bromo and iodo.

"Haloalkyl" and "haloaryl" refer generically to alkyl and aryl radicals that are substituted with one or more halogens, respectively. By way of example "dihaloaryl," "dihaloalkyl," "trihaloaryl" etc. refer to aryl and alkyl substituted with a plurality of halogens, but not necessarily a plurality of the same halogen; thus 4-chloro-3-fluorophenyl is a dihaloaryl group.

"Haloalkyloxy" refers to the group —O-alkyl, where alkyl is as defined herein, and further, alkyl is substituted with one or more halogens. By way of example, a halo$C_{1-3}$alkyloxy" group includes —$OCF_3$, —$OCF_2H$, —$OCHF_2$, —$OCH_2CH_2Br$, —$OCH_2CH_2CH_2I$, —$OC(CH_3)_2Br$, —$OCH_2Cl$ and the like.

"Heteroalkyl" refers to an alkyl where one or more, but not all, carbons are replaced with a heteroatom. A heteroalkyl group has either linear or branched geometry. By way of example, a "2-6 membered heteroalkyl" is a group that can contain no more than 5 carbon atoms, because at least one of the maximum 6 atoms must be a heteroatom, and the group is linear or branched. Also, for the purposes of this invention, a heteroalkyl group always starts with a carbon atom, that is, although a heteroalkyl may contain one or more heteroatoms, the point of attachment to the parent molecule is not a heteroatom. A 2-6 membered heteroalkyl group includes, for example, —$CH_2XCH_3$, —$CH_2CH_2XCH_3$, —$CH_2CH_2XCH_2CH_3$, —$C(CH_2)_2XCH_2CH_3$ and the like, where X is O, NH, N$C_{1-6}$alkyl and S(O)$_{0-2}$, for example.

"Heteroaryl" refers to an aromatic group having from 1 to 10 annular carbon atoms and 1 to 4 annular heteroatoms. Heteroaryl groups have at least one aromatic ring component, but heteroaryls can be fully unsaturated or partially unsaturated. If any aromatic ring in the group has a heteroatom, then the group is a heteroaryl, even, for example, if other aromatic rings in the group have no heteroatoms. For example, 2H-pyrido[3,2-b][1,4]oxazin-3(4H)-one-7-yl, indolyl and benzimidazolyl are "heteroaryls." Heteroaryl groups can have a single ring (e.g., pyridinyl, imidazolyl or furyl) or multiple condensed rings (e.g., indolizinyl, quinolinyl, benzimidazolyl or benzothienyl), where the condensed rings may or may not be aromatic and/or contain a heteroatom, provided that the point of attachment to the parent molecule is through an atom of the aromatic portion of the heteroaryl group. In one embodiment, the nitrogen and/or sulfur ring atom(s) of the heteroaryl group are optionally oxidized to provide for the N-oxide (N→O), sulfinyl, or sulfonyl moieties. Compounds described herein containing phosphorous, in a heterocyclic ring or not, include the oxidized forms of phosphorous. Heteroaryl groups are monocyclic, bicyclic, tricyclic or tetracyclic.

"Heteroarylene" generically refers to any heteroaryl that has at least two groups attached thereto. For a more specific example, "pyridylene" refers to a divalent pyridyl ring radical. A pyridylene, thus can have more than two groups attached, but is defined by a minimum of two non-hydrogen groups attached thereto.

"Heteroaryloxy" refers to —O-heteroaryl.

"Heteroatom" refers to O, S, N, or P.

"Heterocyclyl" in the broadest sense includes aromatic and non-aromatic ring systems and more specifically refers to a stable three- to fifteen-membered ring radical that consists of carbon atoms and from one to five heteroatoms. For purposes of this invention, the heterocyclyl radical can be a monocyclic, bicyclic or tricyclic ring system, which can include fused or bridged ring systems as well as spirocyclic systems; and the nitrogen, phosphorus, carbon or sulfur atoms in the heterocyclyl radical can be optionally oxidized to various oxidation states. In a specific example, the group —S(O)$_{0-2}$—, refers to —S— (sulfide), —S(O)— (sulfoxide), and —SO$_2$— (sulfone) linkages. For convenience, nitrogens, particularly but not exclusively, those defined as annular aromatic nitrogens, are meant to include their corresponding N-oxide form, although not explicitly defined as such in a particular example. Thus, for a compound having, for example, a pyridyl ring; the corresponding pyridyl-N-oxide is meant to be included in the presently disclosed compounds. In addition, annular nitrogen atoms can be optionally quaternized. "Heterocycle" includes heteroaryl and heteroalicyclyl, that is a heterocyclic ring can be partially or fully saturated or aromatic. Thus a term such as "heterocyclylalkyl" includes heteroalicyclylalkyls and heteroarylalkyls. Examples of heterocyclyl radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, diazabicycloheptane, diazapane, diazepine, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Heterocyclylalkyl" refers to a heterocyclyl group linked to the parent structure via, e.g., an alkylene linker, for example (tetrahydrofuran-3-yl)methyl- or (pyridin-4-yl) methyl

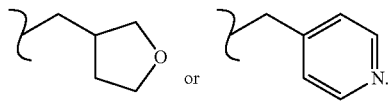

"Heterocyclyloxy" refers to the group —O-heterocycyl.

"Hydroxy" or "hydroxyl" refers to the group —OH.

"Hydroxyalkyl" refers to a hydroxy-substituted alkyl group, e.g., —(CH$_2$)$_x$OH.

"JAK inhibitor" refers to a compound that inhibits at least one member of the Janus kinase family. The Janus kinase (JAK) family is a recognized family of non-receptor tyrosine kinases. Mammals have four members of this family, JAK1, JAK2, JAK3 and Tyrosine kinase 2 (TYK2). Phosphorylated JAK kinases bind various STAT (Signal Transducer and Activator of Transcription) proteins. STAT proteins, which are DNA binding proteins activated by phosphorylation of tyrosine residues, function both as signaling molecules and transcription factors and ultimately bind to specific DNA sequences present in the promoters of cytokine-responsive genes (Leonard et al., (2000), *J. Allergy Clin. Immunol.* 105:877-888). JAK/STAT signaling has been implicated in the mediation of many abnormal immune responses. Studies suggest that JAK3 associates with the common gamma (γc) chain of the various cytokine receptors. JAK3 in particular selectively binds to receptors and is part of the cytokine signaling pathway for IL-2, IL-4, IL-7, IL-9, IL-15 and IL-21. JAK1 interacts with, among others, the receptors for cytokines IL-2, IL-4, IL-7, IL-9, IL-13 and IL-21, while JAK2 interacts with, among others, the receptors for IL-9, IL-13 and TNF-α. Methods for determining JAK inhibition are well known in the art and can be performed, for example, using kits or services commercially available from Ambit Biosciences, Invitrogen and others. Typically JAK inhibitors described herein have an IC50 for at least one member of the JAK family of less than about 10 μM, such as less than 5 μM, such as up to about 1 μM or less than about 100 nM.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 12th Ed., Pergamon Press, Gilman et al. (eds), 1990 which is herein incorporated by reference). The metabolite of a compound described herein or its salt can itself be a biologically active compound in the body. While a prodrug described herein would meet this criteria, that is, form a described biologically active parent compound in vivo, "metabolite" is meant to encompass those compounds not contemplated to have lost a progroup, but rather all other compounds that are formed in vivo upon administration of a compound of the invention which retain the biological activities described herein. Thus one aspect disclosed compounds specifically contemplated herein is a metabolite of a compound described herein. For example, a biologically active metabolite is discovered serendipitously, that is, no prodrug design per se was undertaken. Stated another way, biologically active compounds inherently formed as a result of practicing methods of the invention, are contemplated and disclosed herein.

"Nitro" refers to the group —NO$_2$.

"Optional" or "optionally" means that the subsequently described event or circumstance may or may not occur, and that the description includes instances where said event or circumstance occurs and instances in which it does not. One of ordinary skill in the art would understand that, with respect to any molecule described as containing one or more optional substituents, that only synthetically feasible compounds are meant to be included. "Optionally substituted" refers to all subsequent modifiers in a term, for example in the term "optionally substituted aryl$C_{1-8}$alkyl," optional substitution may occur on both the "$C_{1-8}$alkyl" portion and the "aryl" portion of the aryl$C_{1-8}$alkyl group. Also by way of example, optionally substituted alkyl includes optionally substituted cycloalkyl groups. The term "substituted," when used to modify a specified group or radical, means that one or more hydrogen atoms of the specified group or radical are each, independently of one another, replaced with the same or different substituent groups as defined below. Thus, when a group is defined as "optionally substituted" the definition is meant to encompass when the groups is substituted with one or more of the radicals defined below, and when it is not so substituted.

"Oxo" refers to a double bond oxygen radical, =O.

"Oxy" refers to —O. radical (also designated as →O), that is, a single bond oxygen radical. By way of example, N-oxides are nitrogens bearing an oxy radical.

"Patient" or "Subject" refers to mammals and other animals, particularly humans. Thus the methods are applicable to both human therapy and veterinary applications. In one embodiment the patient or subject is a mammal. In another embodiment the patient or subject is a human.

"Perhalo" as a modifier means that the group so modified has all its available hydrogens replaced with halogens. An example would be "perhaloalkyl." Perhaloalkyls include —$CF_3$, —$CF_2CF_3$, perchloroethyl and the like.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. Pharmaceutically acceptable acid addition salts are those salts that retain the biological effectiveness of the free bases while formed by acid partners that are not biologically or otherwise undesirable, e.g., inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Pharmaceutically acceptable base addition salts include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19, which is incorporated herein by reference.) Additional examples of suitable salts, without limitation, include citrate salts and xinafoate salts.

"Pharmaceutically effective amount" and "therapeutically effective amount" refer to an amount of a compound sufficient to treat a specified disorder or disease or one or more of its symptoms and/or to prevent the occurrence of the disease or disorder. The amount of a compound which constitutes a "therapeutically effective amount" will vary depending on the compound, the disease state and its severity, the age of the subject to be treated, and the like. The therapeutically effective amount can be determined routinely by one of ordinary skill in the art.

"Prodrug" refers to compounds that are transformed in vivo to yield the parent compound, for example, by hydrolysis in the gut or enzymatic conversion in blood. The prodrug includes at least one functional group masked with a progroup or promoiety, which may be cleaved under conditions of use. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) where the alkyl group is a straight or branched chain, and phosphates. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention can be prepared according to conventional methods. A thorough discussion of prodrugs is provided in T. Higuchi and V. Stella, "Pro-drugs as Novel Delivery Systems," Vol 14 of the A.C.S. Symposium Series, and in *Bioreversible Carriers in Drug Design*, ed. Edward B. Roche, American Pharmaceutical Association and Pergamon Press, 1987, both of which are incorporated herein by reference for all purposes.

"Second Therapeutic (Agent)" as used herein concerns any additional compound, drug, or formulation that can be used with disclosed embodiments of the compound described here, particularly those agents used to aid in ventilating a subject. Particular examples of a second therapeutic agents are disclosed herein.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. The compounds described herein can exist in unsolvated as well as solvated forms with solvents, pharmaceutically acceptable or not, such as water, ethanol, and the like. Solvated forms of the presently disclosed compounds are contemplated herein and are encompassed by the invention, at least in generic terms.

"Stereoisomer" and "stereoisomers" refer to compounds that have the same atomic connectivity but different atomic arrangement in space. Stereoisomers include cis-trans isomers, E and Z isomers, enantiomers and diastereomers.

Compounds of the invention, or their pharmaceutically acceptable salts can contain one or more asymmetric centers and can thus give rise to enantiomers, diastereomers, and other stereoisomeric forms that can be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers can be prepared using chiral synthons, chiral reagents, or resolved using conventional techniques, such as by: formation of diastereoisomeric salts or complexes which can be separated, for example, by crystallization; via formation of diastereoisomeric derivatives which can be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer can be synthesized by asymmetric synthesis using optically active reagents, substrates, catalysts or solvents, or by converting on enantiomer to the other by asymmetric transformation. For a mixture of enantiomers, enriched in a particular enantiomer, the major component enantiomer can be further enriched (with concomitant loss in yield) by recrystallization.

When the compounds described herein contain olefinic double bonds or other centers of geometric asymmetry, and unless specified otherwise, it is intended that the compounds include both E and Z geometric isomers.

A "substituent" is an atom or group of atoms that replaces another atom in a molecule as the result of a reaction. The term "substituent" typically refers to an atom or group of atoms that replaces a hydrogen atom on a parent hydrocarbon chain or ring. Unless stated explicitly otherwise, all functional groups described herein may be unsubstituted or substituted with one or more substituent groups. For example, the term "alkyl" refers to both substituted and unsubstituted alkyl groups. Substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —N(R$^{80}$)$_2$, perhaloalkyl, —CN, —OCN, —SCN, —NO, —NO$_2$, =N$_2$, —N$_3$, —SO$_2$R$^{70}$, —SO$_3$$^-$M$^+$, —SO$_3$R$^{70}$, —OSO$_2$R$^{70}$, —OSO$_3$$^-$M$^+$, —OSO$_3$R$^{70}$, —OP(O)(O$^-$)$_2$(M$^+$)$_2$, —OP(O) (O$^-$)$_2$M$^{2+}$, —OP(O)(OR$^{70}$)O$^-$M$^+$, —OP(O)(OR$^{70}$)$_2$, —P(O)(O$^-$)$_2$(M$^+$)$_2$, —P(O)(O$^-$)$_2$M$^{2+}$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2$$^-$M$^+$, —CO$_2$R$^{70}$, —C(S)OR$^{70}$, —C(O)N(R$^{80}$)$_2$, —C(NR$^{70}$)(R$^{80}$)$_2$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)N(R$^{80}$)$_2$, —NR$^{70}$C(NR$^{70}$)R$^{70}$ and —NR$^{70}$C(NR$^{70}$)N(R$^{80}$)$_2$, where R$^{60}$ is C$_{1-6}$alkyl, 3 to 10-membered heterocyclyl, 3 to 10-membered heterocyclylC$_{1-6}$alkyl, C$_{6-10}$aryl or C$_{6-10}$arylC$_{1-6}$alkyl; each R$^{70}$ is independently for each occurrence hydrogen or R$^{60}$; each R$^{80}$ is independently for each occurrence R$^{70}$ or alternatively, two R$^{80}$'s, taken together with the nitrogen atom to which they are bonded, form a 3 to 7-membered heteroalicyclyl which optionally includes from 1 to 4 of the same or different additional heteroatoms selected from O, N and S, of which N optionally has H or C$_1$-C$_3$alkyl substitution; and each M$^+$ is a counter ion with a net single positive charge. Each M$^+$ is independently for each occurrence, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ (a "subscript 0.5 means e.g. that one of the counter ions for such divalent alkali earth ions can be an ionized form of a compound of the invention and the other a typical counter ion such as chloride, or two ionized compounds can serve as counter ions for such divalent alkali earth ions, or a doubly ionized compound can serve as the counter ion for such divalent alkali earth ions). As specific examples, —N(R$^{80}$)$_2$ is meant to include —NH$_2$, —NH-alkyl, —NH-pyrrolidin-3-yl, N-pyrrolidinyl, N-piperazinyl, 4N-methyl-piperazin-1-yl, N-morpholinyl and the like.

Substituent groups for replacing hydrogens on unsaturated carbon atoms in groups containing unsaturated carbons are, unless otherwise specified, —R$^{60}$, halo, —O$^-$M$^+$, —OR$^{70}$, —SR$^{70}$, —S$^-$M$^+$, —N(R$^{80}$)$_2$, perhaloalkyl, —CN, —OCN, —SCN, —NO, —NO$_2$, —N$_3$, —SO$_2$R$^{70}$, —SO$_3$$^-$M$^+$, —SO$_3$R$^{70}$, —OSO$_2$R$^{70}$, —OSO$_3$$^-$M$^+$, —OSO$_3$R$^{70}$, —PO$_3$$^{2-}$(M$^+$)$_2$, —PO$_3$$^{2-}$M$^{2+}$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2$$^-$M$^+$, —CO$_2$R$^{70}$, —C(S)OR$^{70}$, —C(O)NR$^{80}$R$^{80}$, —C(NR$^{70}$)N(R$^{80}$)$_2$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)N(R$^{80}$)$_2$, —NR$^{70}$C(NR$^{70}$)R$^{70}$ and —NR$^{70}$C(NR$^{70}$)N(R$^{80}$)$_2$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

Substituent groups for replacing hydrogens on nitrogen atoms in groups containing such nitrogen atoms are, unless otherwise specified, —R$^{60}$, —O$^-$M$^+$, —OR$^{70}$, —SR$^{70}$, —S$^-$M$^+$, —N(R$^{80}$)$_2$, perhaloalkyl, —CN, —NO, —NO$_2$, —S(O)$_2$R$^{70}$, —SO$_3$$^-$M$^+$, —SO$_3$R$^{70}$, —OS(O)$_2$R$^{70}$, —OSO$_3$$^-$M$^+$, —OSO$_3$R$^{70}$, —PO$_3$$^{2-}$(M$^+$)$_2$, —PO$_3$$^{2-}$M$^{2+}$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC$_2$R$^{70}$, —OC(S)OR$^{70}$, —NR$^{70}$C(O)R$^{70}$, —NR$^{70}$C(S)R$^{70}$, —NR$^{70}$CO$_2$R$^{70}$, —NR$^{70}$C(S)OR$^{70}$, —NR$^{70}$C(O)N(R$^{80}$)$_2$, —NR$^{70}$C(NR$^{70}$)R$^{70}$ and —NR$^{70}$C(NR$^{70}$)N(R$^{80}$)$_2$, where R$^{60}$, R$^{70}$, R$^{80}$ and M$^+$ are as previously defined.

In one embodiment, a group that is substituted has 1, 2, 3, or 4 substituents, 1, 2, or 3 substituents, 1 or 2 substituents, or 1 substituent.

It is understood that in all substituted groups, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such case that the language permits such multiple substitutions, the maximum number of such iterations of substitution is three.

"Suitable leaving group" is defined as the term would be understood by one of ordinary skill in the art; that is, a group on a carbon, where upon reaction a new bond is to be formed, the carbon loses the group upon formation of the new bond. A typical example employing a suitable leaving group is a nucleophilic substitution reaction, e.g., on a sp$^3$ hybridized carbon (SN$_2$ or SN$_1$), e.g. where the leaving group is a halide, such as a bromide, the reactant might be benzyl bromide. Another typical example of such a reaction is a nucleophilic aromatic substitution reaction (SNAr). Another example is an insertion reaction (for example by a transition metal) into the bond between an aromatic reaction partner bearing a leaving group followed by reductive coupling. "Suitable leaving group" is not limited to such mechanistic restrictions. Examples of suitable leaving groups include halogens, optionally substituted aryl or alkyl sulfonates, phosphonates, azides and —S(O)$_{0-2}$R where R is, for example optionally substituted alkyl, optionally substituted aryl, or optionally substituted heteroaryl. Those of skill in the art of organic synthesis will readily identify suitable leaving groups to perform a desired reaction under different reaction.

"Sulfonamide" refers to the group —SO$_2$NH$_2$, —N(H)SO$_2$H, —N(H)SO$_2$alkyl, —N(H)SO$_2$aryl, or —N(H)SO$_2$heterocyclyl.

"Sulfonyl" refers to the group —SO$_2$H, —SO$_2$alkyl, —SO$_2$aryl, or —SO$_2$heterocyclyl.

"Sulfanyl" refers to the group: —SH, —S-alkyl, —S-aryl, or —S-heterocyclyl.

"Sulfinyl" refers to the group: —S(O)H, —S(O)alkyl, —S(O)aryl or —S(O)heterocyclyl.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible and contemplated herein.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, for example, arresting or slowing its development;

(iii) relieving the disease or condition, for example, causing regression of the disease or condition or a symptom thereof; or (iv) stabilizing the disease or condition.

As used herein, the terms "disease" and "condition" can be used interchangeably or can be different in that the particular malady or condition may not have a known causative agent (so that etiology has not yet been worked out) and it is therefore not yet recognized as a disease but only as an undesirable condition or syndrome, where a more or less specific set of symptoms have been identified by clinicians.

Similarly, it is understood that the above definitions are not intended to include impermissible substitution patterns (e.g., methyl substituted with 5 fluoro groups). Such impermissible substitution patterns are easily recognized by a person having ordinary skill in the art.

II. Autoimmune Diseases

Autoimmune diseases result from an inappropriate immune response, and may involve tissue injury that occurs as a result of a humoral and/or cell-mediated response to immunogens or antigens of endogenous and/or exogenous origin. JAK inhibitors, such as the 2,4-substituted pyrimidinediamine compounds described herein, can be used to treat and/or prevent certain autoimmune diseases, such as Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, membranous glomerulopathy, Reiter's syndrome, polymyositis-dermatomyositis, systemic sclerosis, polyarteritis nodosa, multiple sclerosis, bullous pemphigoid, Cogan's syndrome, ankylosing spondylitis, Wegener's granulomatosis, autoimmune alopecia, and inflammatory bowel diseases, such as Crohn's disease, collagenous colitis, granulomatous ileocolitis, idiopathic inflammatory bowel disease, ileitis, irritable bowel syndrome, lymphocytic colitis, regional enteritis, spastic colon, and ulcerative colitis. In particular embodiments, the methods may be used to treat or prevent inflammatory bowel diseases, such as Crohn's disease, collagenous colitis, granulomatous ileocolitis, idiopathic inflammatory bowel disease, ileitis, irritable bowel syndrome, lymphocytic colitis, regional enteritis, spastic colon, and ulcerative colitis. In some examples, the inflammatory bowel disease is ulcerative colitis, Crohn's disease, lymphocytic colitis, or collagenous colitis.

It will be appreciated by skilled artisans that many of the above-listed diseases are associated with severe symptoms, the amelioration of which provides significant therapeutic benefit even in instances where the underlying disease may not be ameliorated.

III. Compounds and Compositions Thereof

A. Compounds

The present disclosure concerns compounds capable of treating and/or preventing certain diseases, such as inflammatory bowel diseases. Embodiments of the disclosed compounds are JAK inhibitors. Because JAK3 is required for immune cell development, targeting JAK3 is a useful strategy for treating inflammatory bowel diseases. The selectivity of JAK3 inhibitors has advantages over currently used drugs, which have many biological targets and diverse side effects.

The compounds, and other forms thereof, including, by way of example and without limitation, salts, hydrates, solvates, N-oxides and prodrugs, described herein are generally 2,4-pyrimidinediamines. Certain disclosed compounds are pyrimidinediamines substituted at the 5-position with various groups; substituted at the 2-amine with various aromatic groups; and/or substituted at the 4-amine with heteroaryl groups, such as a heterobicyclic group, exemplified by benzo[d]oxazol-2(3H)-one, which itself may comprise one or more groups, including prodrug moieties, as described herein.

More specifically, exemplary disclosed compounds are described in terms of formula I:

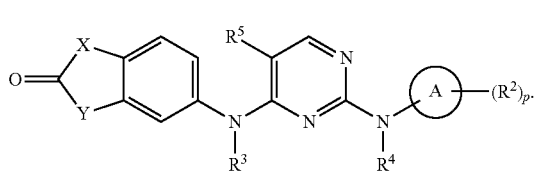

With reference to formula I, X and Y independently are heteroatoms or heteroatom-containing groups, particularly O or $NR^1$; each $R^1$ is independently H or alkyl, particularly lower alkyl, such as $C_1$-$C_6$ alkyl; ring A is aryl, such as phenyl, heteroaryl, such as pyridyl, or a fused ring system, such as, by way of example, an indazole ring system; each $R^2$ independently is H, alkyl, alkoxy, amide, cyano, halo, haloalkyl, hydroxyalkyl, heteroalkyl, heterocyclyl, sulfonyl, sulfonamide, or two $R^2$ groups, taken together with the atom or atoms to which they are attached, combine to form a 4-10 membered ring system, such as a partially or fully saturated monocyclic ring, or ring system comprising two or more ring systems, including bicyclic ring systems, tricyclic ring systems, and the like, and particularly including fused ring systems, such as bicyclic fused ring systems; p is 0, 1, 2, 3 or 4, more typically 1, 2 or 3; $R^3$ and $R^4$ independently are selected from H and alkyl, particularly lower alkyl, such as $C_1$-$C_6$ alkyl, and more typically methyl; and $R^5$ is selected from halo, particularly fluoro, cyano, and alkyl, particularly lower alkyl, such as $C_1$-$C_6$ alkyl, and more typically methyl.

In some embodiments according to structural formula I, ring A is a phenyl. In certain embodiments, ring A is phenyl with at least one $R^2$ group para or meta to N2 of the pyrimidinediamine, or ring A is phenyl and two $R^2$ groups, taken together with the atom or atoms to which they are attached, combine to form a 4-10 membered bicyclic ring system with ring A.

As mentioned, certain presently disclosed compounds have structural formula I where ring A is phenyl, including phenyl optionally substituted with one or more $R^2$ groups, each of which are optionally substituted with one or more groups. Thus, in one embodiment, disclosed compounds have formula II:

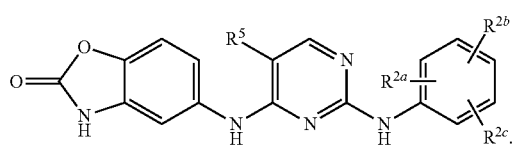

II

With reference to formula II, $R^{2a}$, $R^{2b}$, and $R^{2c}$ independently are H, alkyl, alkoxy, amide, cyano, halo, haloalkyl, hydroxyalkyl, heteroalkyl, heterocyclyl, sulfonyl, sulfonamide, or two of the $R^{2a-c}$ groups, taken together with the atom or atoms to which they are attached, combine to form a 4-10 membered ring system, such as a partially or fully saturated monocyclic ring, or ring system comprising two or more ring systems, including bicyclic ring systems, tricyclic ring systems, and the like, and particularly including fused ring systems, such as bicyclic fused ring systems; and $R^5$ is selected from halo, particularly fluoro, cyano, and alkyl, such as $C_1$-$C_6$ alkyl, and more typically methyl.

In other embodiments, the compound may have a formula III:

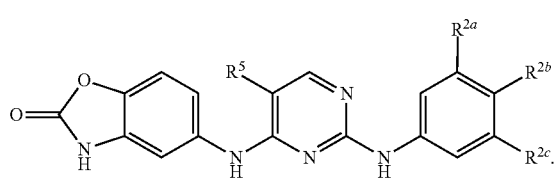

III

With reference to formula III, $R^{2a}$, $R^{2b}$, and $R^{2c}$ independently are H, alkyl, alkoxy, amide, cyano, halo, haloalkyl, hydroxyalkyl, heteroalkyl, heterocyclyl, sulfonyl, sulfonamide, or two $R^{2a-c}$ groups, taken together with the atom or atoms to which they are attached, combine to form a 4-10 membered ring system, such as a partially or fully saturated monocyclic ring, or ring system comprising two or more ring systems, including bicyclic ring systems, tricyclic ring systems, and the like, and particularly including fused ring systems, such as bicyclic fused ring systems; and $R^5$ is halo, particularly fluoro, cyano, and alkyl, such as $C_1$-$C_6$ alkyl, and more typically methyl. In particular embodiments, $R^{2a}$ and $R^{2c}$ independently are H and $R^{2b}$ is an amide. In other disclosed embodiments, $R^{2a}$ and $R^{2b}$ independently are H and $R^{2c}$ is selected from sulfonamide, sulfonyl, and heteroalkyl.

In certain embodiments, the compound may be a prodrug according to formula IV:

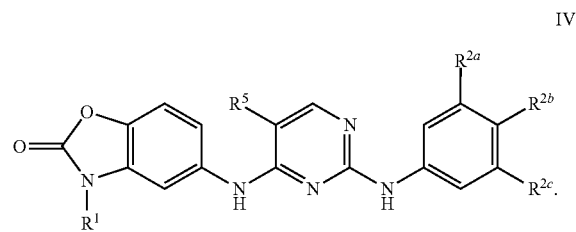

IV

With reference to formula IV, $R^1$ is a progroup, such as —$CH_2OP(O)(ONa)_2$; $R^{2a}$, $R^{2b}$, and $R^{2c}$ independently are H, alkyl, alkoxy, amide, cyano, halo, haloalkyl, hydroxyalkyl, heteroalkyl, heterocyclyl, sulfonyl, sulfonamide, or two $R^{2a-c}$ groups, taken together with the atom or atoms to which they are attached, combine to form a 4-10 membered ring system, such as a partially or fully saturated monocyclic ring, or ring system comprising two or more ring systems, including bicyclic ring systems, tricyclic ring systems, and the like, and particularly including fused ring systems, such as bicyclic fused ring systems; and $R^5$ is halo, particularly fluoro, cyano, and alkyl, such as $C_1$-$C_6$ alkyl, and more typically methyl.

A person of ordinary skill in the art will recognize that any one of the groups described herein for the general formulas may be substituted with one or more substituents. The term "substituted" means that one or more hydrogen atoms of the specified group or radical are each, independently of one another, replaced with the same or different substituent groups as defined in the definitions section for "substituent groups for substituting for one or more hydrogen atoms." The presently disclosed compounds can exist as the parent compound, or a prodrug or pharmaceutically acceptable salt thereof, all of which can be in the form of hydrates, solvates, and N-oxides, as will be understood by a person or ordinary skill in the art. One embodiment is a pharmaceutically acceptable salt form of a compound of formula I. The pharmaceutically acceptable salts of the present invention can be formed by any acceptable method such as, by way of example: reacting the free base form of the product with one or more equivalents of the appropriate acid in a solvent or medium in which the salt is insoluble or in a solvent such as water which is removed in vacuo; by freeze drying; or by exchanging the anions of an existing salt for another anion on a suitable ion exchange resin. The present invention includes within its scope solvates of the disclosed compounds and salts, such as hydrates of the compounds and their salts, for example, a hydrated formate salt or a hydrated xinafoate salt.

In particular examples, the compounds include those shown below in Table 1.

TABLE 1

| Compound Number | Structure | Name |
|---|---|---|
| A1 | 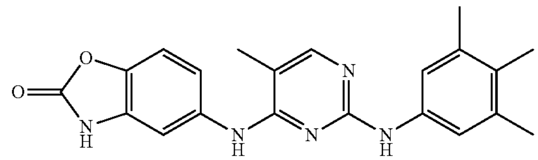 [SMILES: Cc1cnc(Nc2cc(C)c(C)c(C)c2)nc1Nc1ccc2oc(=O)[nH]c2c1] | N2-(3,4,5-trimethyl)phenyl-5-methyl-N4-(2-oxo-2,3-dihydro-1,3-benzoxazol-5-yl)-2,4-pyrimidinediamine |
| A2 | 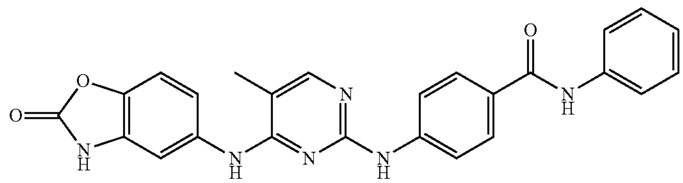 [SMILES: Cc1cnc(Nc2ccc(C(=O)Nc3ccccc3)cc2)nc1Nc1ccc2oc(=O)[nH]c2c1] | 4-[5-methyl-4-(2-oxo-2,3-dihydro-benzoxazol-5-ylamino)-pyrimidin-2-ylamino]-N-phenyl-benzamide |
| A3 | 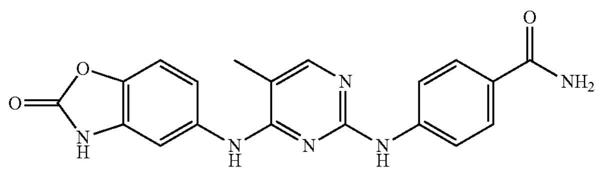 [SMILES: Cc1cnc(Nc2ccc(C(N)=O)cc2)nc1Nc1ccc2oc(=O)[nH]c2c1] | N4-(benzo[d]oxazol-2(3H)-on-5-yl)-N2-(4-aminocarbonylphenyl)-5-methylpyrimidine-2,4-diamine |
| A4 | 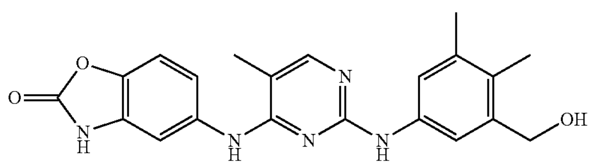 [SMILES: Cc1cnc(Nc2cc(C)c(C)c(CO)c2)nc1Nc1ccc2oc(=O)[nH]c2c1] | N2-(3,4-dimethyl-5-hydroxymethyl)phenyl-5-methyl-N4-(2-oxo-2,3-dihydro-1,3-benzoxazol-5-yl)-2,4-pyrimidinediamine |
| A5 | 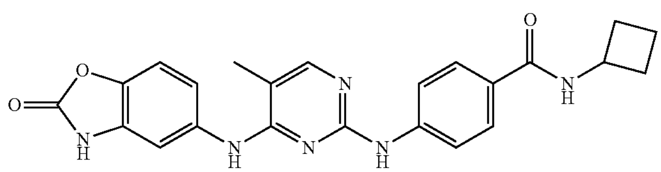 [SMILES: Cc1cnc(Nc2ccc(C(=O)NC3CCC3)cc2)nc1Nc1ccc2oc(=O)[nH]c2c1] | N-cyclobutyl-4-[5-methyl-4-(2-oxo-2,3-dihydro-benzooxazol-5-ylamino)-pyrimidin-2-ylamino]-benzamide |
| A6 | 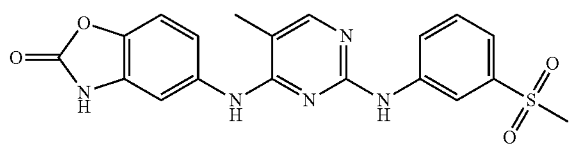 [SMILES: Cc1cnc(Nc2cccc(S(C)(=O)=O)c2)nc1Nc1ccc2oc(=O)[nH]c2c1] | N4-(benzo[d]oxazol-2(3H)-on-5-yl)-N2-(3-methylsulfonyl)phenyl)-5-methylpyrimidine-2,4-diamine |
| A7 | 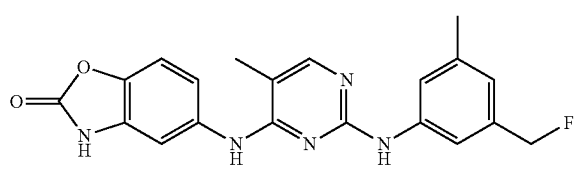 [SMILES: Cc1cc(CF)cc(Nc2ncc(C)c(Nc3ccc4oc(=O)[nH]c4c3)n2)c1] | 5-(2-(3-(fluoromethyl)-5-methylphenylamino)-5-methylpyrimidin-4-ylamino)benzo[d]oxazol-2(3H)-one |
| A8 | 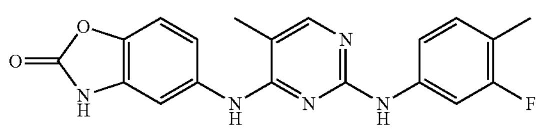 [SMILES: Cc1ccc(Nc2ncc(C)c(Nc3ccc4oc(=O)[nH]c4c3)n2)cc1F] | N2-(3-fluoro-4-methyl)phenyl-5-methyl-N4-(2-oxo-2,3-dihydro-1,3-benzoxazol-5-yl)-2,4-pyrimidinediamine |
| A9 | 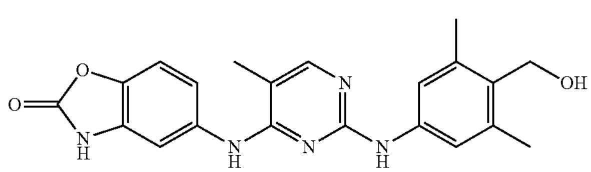 [SMILES: Cc1cnc(Nc2cc(C)c(CO)c(C)c2)nc1Nc1ccc2oc(=O)[nH]c2c1] | N2-(3,5-dimethyl-4-hydroxymethyl)phenyl-5-methyl-N4-(2-oxo-2,3-dihydro-1,3-benzoxazol-5-yl)-2,4-pyrimidinediamine |

TABLE 1-continued

| Compound Number | Structure | Name |
|---|---|---|
| A10 | 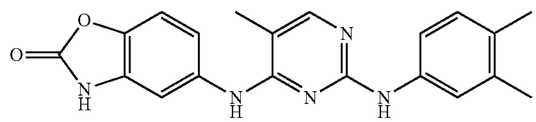 [SMILES: Cc1ccc(Nc2ncc(C)c(Nc3ccc4oc(=O)[nH]c4c3)n2)cc1C] | 5-[2-(3,4-dimethyl-phenylamino)-5-methyl-pyrimidin-4-ylamino]-3H-benzooxazol-2-one |
| A11 | 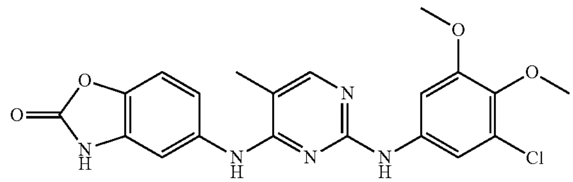 [SMILES: COc1cc(Nc2ncc(C)c(Nc3ccc4oc(=O)[nH]c4c3)n2)cc(Cl)c1OC] | 5-(2-(3-chloro-4,5-dimethoxyphenylamino)-5-methylpyrimidin-4-ylamino)benzo[d]oxazol-2(3H)-one |
| A12 | 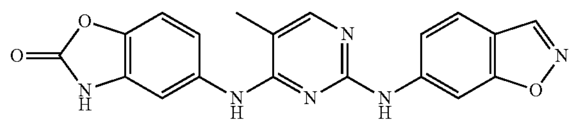 [SMILES: Cc1cnc(Nc2ccc3cnoc3c2)nc1Nc1ccc2oc(=O)[nH]c2c1] | 5-(2-(benzo[d]isoxazol-6-ylamino)-5-methylpyrimidin-4-ylamino)benzo[d]oxazol-2(3H)-one |
| A13 | 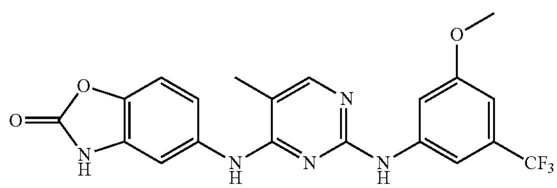 [SMILES: COc1cc(Nc2ncc(C)c(Nc3ccc4oc(=O)[nH]c4c3)n2)cc(C(F)(F)F)c1] | N2-(3-methoxy-5-trifluoromethyl)phenyl-5-methyl-N4-(2-oxo-2,3-dihydro-1,3-benzoxazol-5-yl)-2,4-pyrimidinediamine |
| A14 | 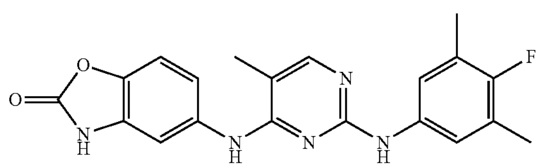 [SMILES: Cc1cnc(Nc2cc(C)c(F)c(C)c2)nc1Nc1ccc2oc(=O)[nH]c2c1] | N2-(3,5-dimethyl-4-fluoro)phenyl-5-methyl-N4-(2-oxo-2,3-dihydro-1,3-benzoxazol-5-yl)-2,4-pyrimidinediamine |
| A15 | 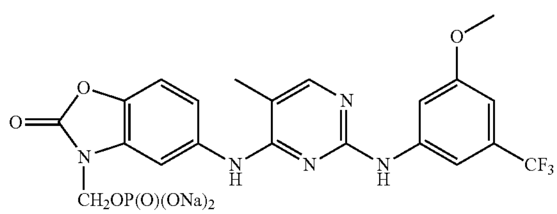 | N2-(3-methoxy-5-trifluoromethyl)phenyl-5-methyl-N4-[3-(phosphonooxy)methyl-2-oxo-2,3-dihydro-1,3-benzoxazol-5-yl]-2,4-pyrimidinediamine bis-sodium salt |
| A16 | 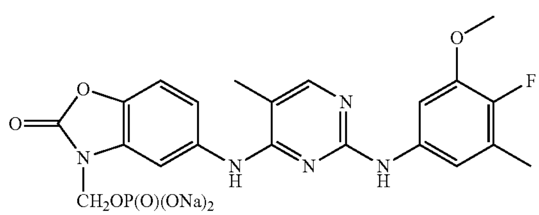 | Sodium (5-(2-(4-fluoro-3-methoxy-5-methylphenylamino)-5-methylpyrimidin-4-ylamino)-2-oxobenzo[d]oxazol-3(2H)-yl)methyl phosphate |
| A17 | 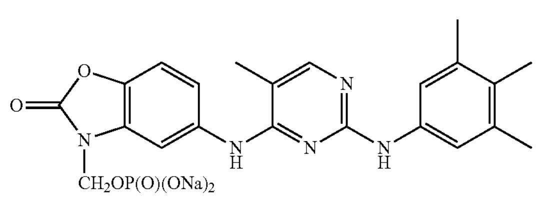 | 5-methyl-N4-[3-(phosphonooxy)methyl-2-oxo-2,3-dihydro-1,3-benzoxazol-5-yl]-N2-(3,4,5-trimethyl)phenyl-2,4-pyrimidinediamine bis-sodium salt |

TABLE 1-continued

| Compound Number | Structure | Name |
|---|---|---|
| A18 | (structure with CH₂OP(O)(ONa)₂ group) | N2-(3,5-dimethyl-4-fluoro)phenyl-5-methyl-N4-[3-(phosphonooxy)methyl-2-oxo-2,3-dihydro-1,3-benzoxazol-5-yl]-2,4-pyrimidinediamine bis-sodium salt |
| I-432 | (structure) | 5-(2-(4-fluoro-3-methoxy-5-methylphenylamino)-5-methylpyrimidin-4-ylamino)benzo[d]oxazol-2(3H)-one |

The compounds and methods of their synthesis are described in PCT Patent Publication Nos. WO 2010/085684 and WO 2012/015972, both of which are incorporated by reference in their entirety herein, and specifically incorporating compound I-432, 5-(2-(4-fluoro-3-methoxy-5-methylphenylamino)-5-methylpyrimidin-4-ylamino)benzo[d]oxazol-2(3H)-one, as disclosed by WO 2010/085684.

B. Prodrugs

Those of skill in the art will appreciate that the compounds described herein can include functional groups that can be masked with progroups to create prodrugs. Such prodrugs are usually, but need not be, pharmacologically inactive until converted into their active drug form. Indeed, at least some of the compounds described herein include promoieties that are hydrolyzable or otherwise cleavable under conditions of use. For example, ester groups commonly undergo acid-catalyzed hydrolysis to yield the parent carboxylic acid when exposed to the acidic conditions of the stomach or base-catalyzed hydrolysis when exposed to the basic conditions of the intestine or blood. Thus, when administered to a subject orally, compounds that include ester moieties can be considered prodrugs of their corresponding carboxylic acid, regardless of whether the ester form is pharmacologically active.

The mechanism by which the progroups metabolize is not critical and can be caused, for example, by hydrolysis under the acidic conditions of the stomach, as described above, and/or by enzymes present in the digestive tract and/or tissues or organs of the body. Indeed, the progroup(s) can be selected to metabolize at a particular site within the body. For example, many esters are cleaved under the acidic conditions found in the stomach. Prodrugs designed to cleave chemically in the stomach to the active compounds can employ progroups including such esters. Alternatively, the progroups can be designed to metabolize in the presence of enzymes such as esterases, amidases, lipolases, and phosphatases, including ATPases and kinase, etc. Progroups including linkages capable of metabolizing in vivo are well known and include, by way of example and not limitation, ethers, thioethers, silylethers, silylthioethers, esters, thioesters, carbonates, thiocarbonates, carbamates, thiocarbamates, ureas, thioureas, and carboxamides. In some instances, a "precursor" group that is oxidized by oxidative enzymes such as, for example, cytochrome $P_{450}$ of the liver, to a metabolizable group, can be selected.

In the prodrugs, any available functional moiety can be masked with a progroup to yield a prodrug. Functional groups within the disclosed compounds that can be masked with progroups for inclusion in a promoiety include, but are not limited to, amines (primary and secondary), hydroxyls, sulfanyls (thiols), and carboxyls. A wide variety of progroups, as well as the resultant promoieties, suitable for masking functional groups in active compounds to yield prodrugs are well-known in the art. For example, a hydroxyl functional group can be masked as a sulfonate, ester, or carbonate promoiety, which can be hydrolyzed in vivo to provide the hydroxyl group. An amino functional group can be masked as an amide, carbamate, imine, urea, phosphenyl, phosphoryl, or sulfenyl promoiety, which can be hydrolyzed in vivo to provide the amino group. A carboxyl group can be masked as an ester (including silyl esters and thioesters), amide, or hydrazide promoiety, which can be hydrolyzed in vivo to provide the carboxyl group. In some embodiments, the progroup is a phosphate-containing progroup of the formula —$(CR^dR^d)_y$—O—P(O)(OH)(OH), or a salt thereof, y is an integer ranging from 1 to 3, typically 1 or 2; and each $R^d$ is, independently of the others, selected from hydrogen, substituted or unsubstituted lower alkyl, substituted or unsubstituted phenyl, substituted or unsubstituted methyl and substituted or unsubstituted benzyl. In a specific embodiment, each $R^d$ is, independently of the others, selected from hydrogen and unsubstituted lower alkyl. Specific exemplary phosphate-containing progroups include —CH₂—O—P(O)(OH)(OH) and —CH₂CH₂—O—P(O)(OH)(OH) and/or the corresponding salts. Other specific examples of suitable progroups and their respective promoieties will be apparent to those of skill in the art. All of these progroups, alone or in combinations, can be included in the prodrugs.

In some embodiments of the disclosed compounds and methods of using the compounds, the progroup(s) can be attached to any available primary or secondary amine, including, for example, the N2 nitrogen atom of the 2,4-pyrimidinediamine, the N4 nitrogen atom of the 2,4-pyrimidinediamine, and/or a primary or secondary nitrogen atom included in a substituent on the 2,4-pyrimidinediamine.

As noted above, the identity of the progroup is not critical, provided that it can be metabolized under the desired conditions of use, for example, under the acidic conditions found in the stomach and/or by enzymes found in vivo, to yield a biologically active group, for example, the compounds as described herein. Thus, skilled artisans will appreciate that the progroup can include virtually any known or later-discovered hydroxyl, amine or thiol protecting group. Non-limiting examples of suitable protecting groups can be found, for example, in *Protective Groups in Organic Synthesis*, Greene & Wuts, $2^{nd}$ Ed., John Wiley & Sons, New York, 1991 (especially pages 10-142 (alcohols), 277-308 (thiols) and 309-405 (amines)), the disclosure of which is incorporated herein by reference.

Compounds A1-A18 inhibit the JAK/Stat pathway. The activity of a specified compound may be assessed in vitro or in vivo. In some embodiments, the activity of a specified compound can be tested in a cellular assay. Suitable assays include assays that determine inhibition of either the phosphorylation activity or ATPase activity of a JAK kinase. Thus, a compound is said to inhibit an activity of a JAK kinase if it inhibits the phosphorylation or ATPase activity of a JAK kinase with an $IC_{50}$ of about 20 µM or less.

One means of assaying for such inhibition is detection of the effect of the 2,4-substituted pyrimidinediamine compounds on the upregulation of downstream gene products. For example, the activity of the disclosed compounds may be characterized by assaying the effect of the 2,4-substituted pyrimidinediamine compounds described herein on the proliferative response of primary human T-cells. In this assay, primary human T-cells derived from peripheral blood and pre-activated through stimulation of the T-cell receptor and CD28, proliferate in culture in response to the cytokine Interleukin-2 (IL-2). This proliferative response is dependent on the activation of JAK1 and JAK3 tyrosine kinases, which phosphorylate and activate the transcription factor Stat-5. The primary human T-cells are incubated with the 2,4-substituted pyrimidinediamine compounds in the presence of IL-2 for 72 hours and at the assay endpoint intracellular ATP concentrations are measured to assess cell viability. A reduction in cell proliferation compared to control conditions is indicative of inhibition of the JAK kinase pathway.

Active compounds as described herein generally inhibit the JAK kinase pathway with an $IC_{50}$ in the range of about 1 mM or less, as measured in the assays described herein. Of course, skilled artisans will appreciate that compounds which exhibit lower $IC_{50}$s, for example on the order of 100 µM, 75 µM, 50 µM, 40 µM, 30 µM, 20 µM, 15 µM, 10 µM, 5 µM, 1 µM, 500 nM, 100 nM, 10 nM, 1 nM, or even lower, may be particularly useful in therapeutic applications. In instances where activity specific to a particular cell type is desired, the compound may be assayed for activity with the desired cell type and counter-screened for a lack of activity against other cell types. The desired degree of "inactivity" in such counter screens, or the desired ratio of activity vs. inactivity may vary for different situations, and may be selected by the user.

C. Pharmaceutical Compositions

In some embodiments a pharmaceutical composition including a compound as described in any of the embodiments herein is administered to a subject. Pharmaceutical compositions described herein can be manufactured by means of conventional mixing, dissolving, granulating, dragee-making, levigating, emulsifying, encapsulating, entrapping, or lyophilization processes. The compositions can be formulated in conventional manner using one or more physiologically acceptable carriers, diluents, excipients, or auxiliaries which facilitate processing of the active compounds into preparations which can be used pharmaceutically. *Remington: The Science and Practice of Pharmacy*, The University of the Sciences in Philadelphia, Editor, Lippincott, Williams, & Wilkins, Philadelphia, Pa., $21^{st}$ Edition (2005).

The disclosed compounds can be formulated in the pharmaceutical compositions per se, or in the form of a hydrate, solvate, N-oxide, or pharmaceutically acceptable salt, as described herein. Typically, such salts are more soluble in aqueous solutions than the corresponding free acids and bases, but salts having lower solubility than the corresponding free acids and bases can also be formed.

One embodiment is a pharmaceutical formulation including at least one of compounds A1-A18, or a prodrug thereof, and at least one pharmaceutically acceptable excipient, diluent, preservative, stabilizer, or mixture thereof.

The compounds can be provided in a variety of formulations and dosages. The compounds can be provided in a pharmaceutically acceptable form, including where the compound can be formulated in the pharmaceutical compositions per se, or in the form of a hydrate, solvate, N-oxide, or pharmaceutically acceptable salt, as described herein. Typically, such salts are more soluble in aqueous solutions than the corresponding free acids and bases, but salts having lower solubility than the corresponding free acids and bases can also be formed. It is to be understood that reference to the compound or "active" in discussions of formulations is also intended to include, where appropriate as known to those of skill in the art, formulation of the prodrugs of the disclosed compounds.

In some embodiments, the compounds are provided as non-toxic, pharmaceutically acceptable salts. Generally, pharmaceutically acceptable salts are those salts that retain substantially one or more of the desired pharmacological activities of the parent compound and which are suitable for administration to humans. Suitable pharmaceutically acceptable salts of the compounds described herein include acid addition salts such as those formed with hydrochloric acid, fumaric acid, p-toluenesulfonic acid, maleic acid, succinic acid, acetic acid, citric acid, tartaric acid, carbonic acid, or phosphoric acid. Salts of amine groups can also include quaternary ammonium salts in which the amino nitrogen atom carries a suitable organic group such as an alkyl, alkenyl, alkynyl, or substituted alkyl moiety. Furthermore, where presently disclosed compounds carry an acidic moiety, suitable pharmaceutically acceptable salts thereof can include metal salts such as alkali metal salts, for example, sodium or potassium salts; and alkaline earth metal salts, for example, calcium or magnesium salts.

The pharmaceutical compositions for the administration of the disclosed compounds can be conveniently presented in dosage unit form and can be prepared by any of the methods well known in the art of pharmacy. The pharmaceutical compositions can be, for example, prepared by uniformly and intimately bringing the active ingredient into association with a liquid carrier, a finely divided solid carrier or both, and then, if necessary, shaping the product into the desired formulation. In the pharmaceutical composition the active object compound is included in an amount sufficient to produce the desired therapeutic effect.

In particular disclosed embodiments, the composition comprises from about 0.0001 to about 100 mg/kg/day, from about 0.001 to about 100 mg/kg/day; or from about 0.01 mg/kg/day to about 100 mg/kg/day of the compound. The composition may also further comprise a pharmaceutically acceptable carrier, selected from lactose, glucose, raffinose, melezitose, lactitol, maltitol, trehalose, sucrose, mannitol, starch, or combinations thereof. In particular disclosed embodiments, the composition comprises about 1 to about 20 total weight percent of the compound and the one or more other therapeutic agents, and about 99 to about 80 weight percent of the pharmaceutically acceptable carrier.

In certain disclosed embodiments, the compound is a dry powder, which may be encapsulated. Typically, the compound has a particle size, which ranges from about 0.4 µm to about 5 µm.

The compounds can be administered by oral, parenteral (for example, intramuscular, intraperitoneal, intravenous, ICV, intracisternal injection or infusion, subcutaneous injection, or implant), inhalation, spray, nasal, vaginal, rectal (for example, rectal suppository or enema), sublingual, urethral (for example, urethral suppository) or topical routes of administration (for example, gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. In addition to the treatment of warm-blooded animals such as mice, rats, horses, cattle, sheep, dogs, cats, and monkeys, the compounds described herein can be used for treating humans.

Administration of the disclosed compounds, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (e.g., intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

Systemic formulations include those designed for administration by injection (for example, subcutaneous, intravenous, intramuscular, intrathecal, or intraperitoneal injection) as well as those designed for transdermal, transmucosal, oral, or pulmonary administration. Useful injectable preparations include sterile suspensions, solutions, or emulsions of the active compound(s) in aqueous or oily vehicles. The compositions can also contain formulating agents, such as suspending, stabilizing, and/or dispersing agents. The formulations for injection can be presented in unit dosage form, for example, in ampules or in multidose containers, and can contain added preservatives. Alternatively, the injectable formulation can be provided in powder form for reconstitution with a suitable vehicle, including but not limited to sterile pyrogen-free water, buffer, and dextrose solution, before use. To this end, the active compound(s) can be dried by any art-known technique, such as lyophilization, and reconstituted prior to use.

For oral administration, the pharmaceutical compositions can take the form of, for example, lozenges, tablets, or capsules prepared by conventional means with pharmaceutically acceptable excipients such as binding agents (for example, pregelatinised maize starch, polyvinylpyrrolidone, or hydroxypropyl methylcellulose); fillers (for example, lactose, microcrystalline cellulose, or calcium hydrogen phosphate); lubricants (for example, magnesium stearate, talc, or silica); disintegrants (for example, potato starch or sodium starch glycolate); or wetting agents (for example, sodium lauryl sulfate). The tablets can be coated by methods well known in the art with, for example, sugars, films, or enteric coatings. Additionally, the pharmaceutical compositions containing at least one of compounds A1-A18 as active ingredient or prodrug thereof in a form suitable for oral use can also include, for example, troches, lozenges, aqueous or oily suspensions, dispersible powders or granules, emulsions, hard or soft capsules, or syrups or elixirs. Compositions intended for oral use can be prepared according to any method known to the art for the manufacture of pharmaceutical compositions, and such compositions can contain one or more agents including sweetening agents, flavoring agents, coloring agents, and preserving agents in order to provide pharmaceutically elegant and palatable preparations. Tablets contain the active ingredient (including drug and/or prodrug) in admixture with non-toxic pharmaceutically acceptable excipients which are suitable for the manufacture of tablets. These excipients can be for example, inert diluents, such as calcium carbonate, sodium carbonate, lactose, calcium phosphate or sodium phosphate; granulating and disintegrating agents (for example, corn starch or alginic acid); binding agents (for example starch, gelatin, or acacia); and lubricating agents (for example, magnesium stearate, stearic acid, or talc). The tablets can be left uncoated or they can be coated by known techniques to delay disintegration and absorption in the gastrointestinal tract and thereby provide a sustained action over a longer period. For example, a time delay material such as glyceryl monostearate or glyceryl distearate can be employed. They can also be coated by the techniques described in the U.S. Pat. Nos. 4,256,108; 4,166,452; and U.S. Pat. No. 4,265,874 to form osmotic therapeutic tablets for control release. The pharmaceutical compositions described herein can also be in the form of oil-in-water emulsions.

Liquid preparations for oral administration can take the form of, for example, elixirs, solutions, syrups, or suspensions, or they can be presented as a dry product for constitution with water or other suitable vehicle before use. Such liquid preparations can be prepared by conventional means with pharmaceutically acceptable additives such as suspending agents (for example, sorbitol syrup, cellulose derivatives, or hydrogenated edible fats); emulsifying agents (for example, lecithin, or acacia); non-aqueous vehicles (for example, almond oil, oily esters, ethyl alcohol, Cremaphor® emulsifying agent, or fractionated vegetable oils); and preservatives (for example, methyl or propyl-p-hydroxybenzoates or sorbic acid). The preparations can also contain buffer salts, preservatives, flavoring, coloring, and sweetening agents as appropriate. Preparations for oral administration can be suitably formulated to give controlled release of the active compound, as is well known. For buccal administration, the compositions can take the form of tablets or lozenges formulated in the conventional manner.

The pharmaceutical compositions can be in the form of a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally-acceptable diluent or solvent. Among the acceptable vehicles and solvents that can be employed are water, Ringer's solution, and isotonic sodium chloride solution.

For rectal routes of administration, the active compound(s) can be formulated as solutions (for retention enemas), suppositories, or ointments containing conventional suppository bases such as cocoa butter or other glycerides.

For transmucosal administration, penetrants appropriate to the barrier to be permeated are used in the formulation. Such penetrants are known in the art.

For topical administration, the disclosed compound(s) or prodrug(s) can be formulated as solutions, gels, ointments, creams, suspensions, etc., as are well-known in the art. Such formulations can be included in a patch or other transdermal delivery system or formulation, for example, a formulation with ingredients specifically designed to aid transport of the compound through the skin and into the body tissues.

For nasal administration or administration by inhalation or insufflation, the active compound(s) or prodrug(s) can be conveniently delivered in the form of a dry powder (either alone, as a mixture, for example in a dry blend with lactose, or as a mixed component particle, for example, mixed with phospholipids, such as phosphatidylcholine) from a dry powder inhaler or as an aerosol spray from pressurized packs or a nebulizer with the use of a suitable propellant (for example, dichlorodifluoromethane, trichlorofluoromethane, dichlorotetrafluoroethane, fluorocarbons, carbon dioxide, or other suitable gas). In the case of a pressurized aerosol, the dosage unit can be determined by providing a valve to deliver a metered amount. Capsules and cartridges for use in an inhaler or insufflator (for example, capsules and cartridges including gelatin) can be formulated containing a powder mix of the compound and a suitable powder base such as lactose or starch. Prior to use in a dry powder or suspension formulation, the drug product typically is micronized to a size suitable for delivery by inhalation (typically less than about 5 microns). This may be achieved as is known to those of skill in the art by an appropriate method, such as spiral jet milling, fluid bed jet milling, supercritical fluid processing, spray drying and the like.

For prolonged delivery, the compound(s) or prodrug(s) can be formulated as a depot preparation for administration by implantation or intramuscular injection. The active ingredient can be formulated with suitable polymeric or hydrophobic materials (for example, as an emulsion in an acceptable oil) or ion exchange resins, or as sparingly soluble derivatives (for example, as a sparingly soluble salt). Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in, for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) can also be employed, although usually at the cost of greater toxicity.

D. Second Therapeutic Agents

Disclosed embodiments of the compound may be administered singly, as compositions comprising one or more of compounds A1-A18, or as compositions comprising the compound and a second therapeutic agent.

In particular disclosed embodiments, the second therapeutic agent may be selected from any of the following:

analgesics—morphine, fentanyl, hydromorphone, oxycodone, codeine, acetaminophen, hydrocodone, buprenorphine, tramadol, venlafaxine, flupirtine, meperidine, pentazocine, dextromoramide, dipipanone;

antibiotics—aminoglycosides (e.g., amikacin, gentamicin, kanamycin, neomycin, netilmicin, tobramycin, and paromycin), carbapenems (e.g., ertapenem, doripenem, imipenem, cilastatin, and meropenem), cephalosporins (e.g., cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, and cefobiprole), glycopeptides (e.g., teicoplanin, vancomycin, and telavancin), lincosamides (e.g., clindamycin and incomysin), lipopeptides) e.g., daptomycin), macrolides (azithromycin, clarithromycin, dirithromycin, erythromycin, roxithromycin, troleandomycin, telithromycin, and spectinomycin), monobactams (e.g., aztreonam), nitrofurans (e.g., furazolidone and nitrofurantoin), penicilllins (e.g., amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, and ticarcillin), penicillin combinations (e.g., amoxicillin/clavulanate, ampicillin/sulbactam, piperacillin/tazobactam, and ticarcillin/clavulanate), polypeptides (e.g., bacitracin, colistin, and polymyxin B), quinolones (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin), sulfonamides (e.g., mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxaxzole), tetracyclines (e.g., demeclocycline, doxycycline, minocycline, oxytetracycline, and tetracycline), antimycobacterial compounds (e.g., clofazimine, dapsone, capreomycin, cycloserine, ethambutol, ethionamide, isoniazid, pyrazinamide, rifampicin (rifampin), rifabutin, rifapentine, and streptomycin), and others. such as arsphenamine, chloramphenicol, fosfomycin, fusidic acid, linezolid, metronidazole, mupirocin, platensimycin, quinuprisin/dalfopristin, rifaximin, thiamphenicol, tigecycline, and tinidazole;

antibodies—anti-TNF-α antibody, e.g., infliximab (Remicade®);

anticoagulants—warfarin (Coumadin®), acenocoumarol, phenprocoumon, atromentin, phenindione, heparin, fondaparinux, idraparinux, rivaroxaban, apixaban, hirudin, lepirudin, bivalirudin, argatrobam, dabigatran, ximelagatran, batroxobin, hementin;

anti-inflammatory agents—steroids, e.g., budesonide, nonsteroidal anti-inflammatory agents, e.g., aminosalicylates (e.g., sulfasalazine, mesalamine, olsalazine, and balsalazide), cyclooxygenase inhibitors (COX-2 inhibitors, such as rofecoxib, celecoxib), diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin;

immunosuppressants—mercaptopurine, corticosteroids such as dexamethasone, hydrocortisone, prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil and azathioprine, and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. Azathioprine is currently available from Salix Pharmaceuticals, Inc. under the brand name Azasan®; mercaptopurine is currently available from Gate Pharmaceuticals, Inc. under the brand name Purinethol®; prednisone and prednisolone are currently available from Roxane Laboratories, Inc.; Methyl prednisolone is currently available from Pfizer; sirolimus (rapamycin) is currently available from Wyeth-Ayerst under the brand name Rapamune®; tacrolimus is currently available from Fujisawa under the brand name Prograf®; cyclosporine is current available from Novartis under the brand dame Sandimmune® and Abbott under the brand name Gengraf®; IMPDH inhibitors such as mycophenolate mofetil and mycophenolic acid are currently available from Roche under the brand name Cellcept® and Novartis under the brand name Myfortic®; azathioprine is currently available from Glaxo Smith Kline under the brand name Imuran®; and antibodies are currently available from Ortho Biotech under the brand name Orthoclone®, Novartis under the brand name Simulect® (basiliximab) and Roche under the brand name Zenapax® (daclizumab).

Guanylate cyclase-C receptor agonists or intestinal secretagogues—for example linaclotide, sold under the name Linzess®.

These various agents can be used in accordance with their standard or common dosages, as specified in the prescribing information accompanying commercially available forms of the drugs (see also, the prescribing information in the 2006 Edition of *The Physician's Desk Reference*), the disclosures of which are incorporated herein by reference.

IV. Method of Use

The disclosed compounds, or compositions thereof, can be used to treat and/or prevent certain autoimmune disorders, such as inflammatory bowel disorders. Compounds A1-A18, prodrug(s) thereof, or compositions thereof, will generally be used in an amount effective to achieve the intended result, for example, in an amount effective to treat or prevent the particular condition being treated.

The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the subject reports an improvement in feeling or condition, notwithstanding that the subject may still be afflicted with the underlying disorder. By prophylactic benefit is meant prevention or delayed onset of a disorder. For prophylactic administration, the compound can be administered to a subject at risk of developing one of the previously described conditions. For example, if it is suspected but unknown whether a subject is susceptible to an inflammatory bowel disease, the compound can be administered prior to the onset of symptoms resulting from the condition. Alternatively, prophylactic administration can be applied to avoid the onset of symptoms in a subject diagnosed with the underlying disorder. For example, a compound can be administered to a genetically predisposed subject prior to expected onset of the disease, such as in the case of an inflammatory bowel disease, e.g., ulcerative colitis or Crohn's disease.

The amount of compound administered will depend upon a variety of factors, including, for example, the particular condition being treated, the mode of administration, whether the desired benefit is prophylactic or therapeutic, the severity of the condition being treated, the age and weight of the subject, the general health of the subject, and/or the bioavailability of the particular active compound. Determination of an effective dosage is well within the capabilities of those skilled in the art.

Dosage, and frequency of administration of the compounds or prodrugs thereof, will also depend on whether the compounds are formulated for treatment of acute episodes of a condition or for the prophylactic treatment of a disorder. A skilled practitioner will be able to determine the optimal dose for a particular individual. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an $IC_{50}$ of the particular compound as measured in an in vitro assay. Calculating dosages to achieve such circulating blood or serum concentrations taking into account the bioavailability of the particular compound is well within the capabilities of skilled artisans. For guidance, the reader is referred to Fingl & Woodbury, "General Principles," In: *Goodman and Gilman's The Pharmaceutical Basis of Therapeutics*, Chapter 1, 12th edition, Pergamon Press, and the references cited therein.

Initial dosages can also be estimated from in vivo data, such as animal models. Animal models useful for testing the efficacy of compounds to treat or prevent the various diseases described above are well-known in the art. Suitable animal models of hypersensitivity or allergic reactions are described in Foster, (1995) *Allergy* 50(21Suppl):6-9, discussion 34-38 and Tumas et al., (2001), *J. Allergy Clin. Immunol.* 107(6):1025-1033. Suitable animal models of allergic rhinitis are described in Szelenyi et al., (2000), *Arzneimittelforschung* 50(11):1037-42; Kawaguchi et al., (1994), *Clin. Exp. Allergy* 24(3):238-244 and Sugimoto et al., (2000), *Immunopharmacology* 48(1):1-7. Suitable animal models of allergic conjunctivitis are described in Carreras et al., (1993), *Br. J. Ophthalmol.* 77(8):509-514; Saiga et al., (1992), *Ophthalmic Res.* 24(1):45-50; and Kunert et al., (2001), *Invest. Ophthalmol. Vis. Sci.* 42(11):2483-2489. Suitable animal models of systemic mastocytosis are described in O'Keefe et al., (1987), *J. Vet. Intern. Med.* 1(2):75-80 and Bean-Knudsen et al., (1989), *Vet. Pathol.* 26(1):90-92. Suitable animal models of hyper IgE syndrome are described in Claman et al., (1990), *Clin. Immunol. Immunopathol.* 56(1):46-53. Suitable animal models of B-cell lymphoma are described in Hough et al., (1998), *Proc. Natl. Acad. Sci. USA* 95:13853-13858 and Hakim et al., (1996), *J. Immunol.* 157(12):5503-5511. Suitable animal models of atopic disorders such as atopic dermatitis, atopic eczema, and atopic asthma are described in Chan et al., (2001), *J. Invest. Dermatol.* 117(4):977-983 and Suto et al., (1999), *Int. Arch. Allergy Immunol.* 120(Suppl 1):70-75. Suitable animal models of transplant rejection, such as models of HVGR, are described in O'Shea et al., (2004), *Nature Reviews Drug Discovery* 3:555-564; Cetkovic-Curlje & Tibbles, (2004), *Current Pharmaceutical Design*

10:1767-1784; and Chengelian et al., (2003), *Science* 302: 875-878. Ordinarily skilled artisans can routinely adapt such information to determine dosages suitable for human administration.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. More typically, the dosage (or effective amount) may range from about 5 mg/kg to about 20 mg/kg; even more typically from about 10 mg/kg to about 20 mg/kg; even more typically from about 15 mg/kg to about 20 mg/kg. Dosage amount and interval can be adjusted individually to provide plasma levels of the compound(s) which are sufficient to maintain therapeutic or prophylactic effect. For example, the compounds can be administered once per week, several times per week (e.g., every other day), once per day, or multiple times per day, depending upon, among other things, the mode of administration, the specific indication being treated, and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

In one embodiment the daily dosage may be greater than zero milligrams per day, such as from about 1 mg/day, up to at least about 2 grams/day. For certain embodiments, the dosage is about 2 mg/day, about 3 mg/day, about 5 mg/day, about 10 mg/day, about 15 mg/day, about 20 mg/day or about 50 mg/day.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The foregoing disclosure pertaining to the dosage requirements for the compounds is pertinent to dosages required for prodrugs, with the realization, apparent to the skilled artisan, that the amount of prodrug(s) administered will also depend upon a variety of factors, including, for example, the bioavailability of the particular prodrug(s) and the conversation rate and efficiency into active drug compound under the selected route of administration. Determination of an effective dosage of prodrug(s) for a particular use and mode of administration is well within the capabilities of those skilled in the art.

Effective dosages can be estimated initially from in vitro activity and metabolism assays. For example, an initial dosage of prodrug for use in animals can be formulated to achieve a circulating blood or serum concentration of the metabolite active compound that is at or above an $IC_{50}$ of the particular compound as measured in an in vitro assay, such as the in vitro CHMC or BMMC and other in vitro assays described in U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO2004/014382), U.S. application Ser. No. 10/903,263 filed Jul. 30, 2004, and international application Serial No. PCT/US2004/24716 (WO2005/016893). Calculating dosages to achieve such circulating blood or serum concentrations, taking into account the bioavailability of the particular prodrug via the desired route of administration, is well within the capabilities of skilled artisans. For guidance, the reader is referred to Fingl & Woodbury, "General Principles," In: *Goodman and Gilman's The Pharmaceutical Basis of Therapeutics*, Chapter 1, 12$^{th}$ edition, Pergamon Press, and the references cited therein.

Particular disclosed embodiments concern a method, comprising administering to a subject one or more of the disclosed compounds in an amount effective to inhibit or prevent a disease, such as an inflammatory bowel disease. For example, the compound(s) may be administered to a subject identified as having an inflammatory bowel disease or being at risk of developing an inflammatory bowel disease. In particular disclosed embodiments, administering comprises exposing the subject to a dosage of the compound that is adjusted to inhibit or prevent the disease. The compound also may be administered alone or as a pharmaceutical composition and typically is administered parenterally (e.g., intravenously, infusion, or implant), orally, or rectally. Additionally, the compound may be administered prophylactically.

The method may further comprise monitoring blood levels of the compound, or a metabolite thereof, in the subject to ascertain the effect of the compound. The method also may further comprise monitoring one or more biomarkers associated with a disease, such as an inflammatory bowel disease.

Thus, in certain embodiments, the method further comprises monitoring one or more biomarkers associated with an inflammatory bowel disease. Suitable biomarkers may include serologic markers such as C-reactive protein, perinuclear antineutrophil cytoplasmic antibody, anti-*Saccharomyces cerevisiae* antibody, anti-OmpC (outer membrane porin C), anti-I2 protein antibody, anti-glycan antibodies, anti-chitobioside IgA, anti-laminaribioside IgG, anti-manobioside IgG, toll-like receptors 2 and 4, β-defensin-1, ubiquitination factor E4A (UBE4A), CXCL16 (a chemokine), resistin, apolipoprotein A-IV; genetic biomarkers such as NOD2/CARD 15, NOD1/CARD4; fecal biomarkers such as fecal calprotectin and lactoferrin; and mucosal biomarkers such as mucosal cytokines and chemokines (e.g., IL-1, IL-1β, IL-4 IL-6, IL-8, IL-10, IL-11, IL13Rα2, IL-15, IL-18, IL-21, IL-23, IL-32, IFN-γ, TNF-α), monocyte chemotactic protein (MCP)-1, RANTES, epithelial neutrophil activating protein 78 (ENA-78)), osteoprotegerin, STC1, PTGS2, IL13Rα2, RelA, A20, pIgR (polymeric immunoglobulin receptor), GR (glucocorticosteroid receptor) expression, CXCL2, CXCL8, CXCL10, calgranulin B, adhesion molecules and markers of activation (e.g., mucosal vascular addressin CAM-1 (MAdCAM-1), NF-κB, mitogen-activated protein kinase (MAPK), ICAM-1, CD40 overexpression, increased phosphorylation of MAPKs (e.g., p38, extracellular signal-regulated kinase and Jun N-terminal kinase)), immune cells (e.g., IL-17-positive cells, TH17 cells, Tregs (regulatory T-cells), neutrophils, monocytes, mucosal dendritic cells, macrophages), non-immune cells (e.g., intestinal epithelial cells with abnormal HLA-DR and/or B7 molecule expression, endothelial cells with high expression of CD146, TLR3, TLR4), matrix metalloproteinases, vascular endothelial growth factor, other mucosal components (e.g., lactate dehydrogenase (LDH) isoenzyme M monomers, LDH 5 monomers, proliferator-activated receptor-2 (PAR2) methylation), mucin 2), and mean histological inflammation.

In particular disclosed embodiments, a method for inhibiting or preventing a disease is contemplated, wherein the method comprises diagnosing a subject in need of treatment for a disease, administering to the subject a compound in an amount effective to inhibit and/or prevent the disease, the compound being selected from any one of the compounds disclosed herein, and permitting the compound to achieve therapeutic benefit for the disease in the subject. In certain embodiments, the disease is an inflammatory bowel disease including, but not limited to, ulcerative colitis, Crohn's disease, lymphocytic colitis, or collagenous colitis.

In particular disclosed embodiments, the method comprises administering one or more disclosed embodiments of the compound, or compositions thereof, to a subject in an amount effective to inhibit or prevent a disease. The compound may have any one of formulas I-IV, such as any one of the exemplary compounds disclosed in Table 1. In some examples, the disease is an inflammatory bowel disease, such as ulcerative colitis.

Typically, administering comprises exposing the subject to a first dose of the one or more compounds, or composition comprising the one or more compounds. The method may further comprise determining a therapeutic blood level of the one or more compounds in the subject, or a therapeutic metabolite blood level of the one or more compounds, in the subject. Additionally, the method may comprise, after determining the therapeutic blood level, adjusting the first dose to a second dose to optimize therapeutic effect. A single compound may be administered serially in plural administrations to the subject, or two or more compounds may be administered either serially or in combination to the subject. In particular disclosed embodiments, the one or more compounds are administered as a pharmaceutical composition. Suitable methods of administration include oral, buccal, mucosal, sublingual, parenteral (e.g., intravenous, intraperitoneal, subcutaneous injection, infusion, implant), intra-arterial, intramuscular, subcutaneous, intraarticular, infusion, intrathecal, intraurethral, topical, subdermal, transdermal, intranasal, inhalation, pulmonary tract, intra-tracheal, intraocular, ocular, intraaural, vaginal, and rectal. In particular disclosed embodiments, the compound is administered parenterally, orally, or rectally. The compound may be administered prophylactically.

The method further may comprise administering a second therapeutic agent to the subject. The second therapeutic may be selected from an analgesic, an antibiotic, an antibody, an anticoagulant, an anti-inflammatory, an immunosuppressant, or combinations thereof. In particular disclosed embodiments, the second therapeutic is administered prior to or subsequent to the one or more compounds. In other embodiments, the second therapeutic is administered in combination with the one or more compounds. The second therapeutic may be selected from any of those disclosed herein. The second therapeutic also may be any other therapeutic that may have a beneficial effect for treating or preventing the disease and/or one or more symptoms associated therewith.

V. Examples

Example 1

Inhibition of IL-13 Signaling

This example describes the effect of exemplary compounds on IL-13 signaling induced ICAM-1 expression and Stat6 phosphorylation in human small airway epithelial cells (SAEC). Exemplary compounds A1-A12 inhibited IL-13 signaling in this example with an $EC_{50}$ of less than or equal to 100 nM. In parallel experiments, the compounds similarly inhibited IL-4 signaling.

ICAM-1 Expression:

Primary human small airway epithelial cells (SAEC) were pre-incubated with compound for 1 hour prior to stimulation IL-13 or IL-4 for 20 hours. The surface expression of ICAM-1 was measured by flow cytometry.

Materials

Small Airway Epithelial Cells (SAEC) (LONZA, Cat# CC-2547)

Small Airway Epithelial Cell Growth Medium SAGM BulletKit™ (LONZA, Cat# CC-3118)

ReagentPack™ Subculture Reagents (LONZA, Cat# CC-5034)

Dimethyl Sulfoxide (DMSO) (Sigma-Aldrich, Cat# D2650)

Human IL-13 (Peprotech, Cat#200-13)

Human IL-4 (Peprotech, Cat# AF-200-04)

FACS buffer: PBS+2% FBS (4° C.)

ICAM-1-APC antibody (BD Biosciences, Cat#559771)

Method

SAEC were seeded at $2 \times 10^5$ cells/100 µL/well in a flat bottom 96-well plate. Compound was serially diluted in DMSO from 5 mM in 3-fold dilutions, and then diluted 3:125 in SAGM. 10 µL of 12× compound was added to the cells per well in duplicate and were preincubated for 1 hour at 37° C., 5% $CO_2$. Cells were then stimulated with 10 µL 12× IL-13 (12.5 ng/mL final) for 20 hours at 37° C., 5% $CO_2$. The media was removed and the cells were briefly trypsinized, the trypsin neutralized with media, and the cells transferred to a round-bottom plate and washed in FACS buffer. The cells were stained for 20 min at 4° C. with 50 µL/well of anti-ICAM-1-APC antibody diluted 1:100 in FACS buffer. The cells were washed with 150 µL of ice-cold FACS buffer, and resuspended in 100 µL of ice-cold FACS buffer for FACS analysis.

Stat6 Phosphorylation:

Primary human small airway epithelial cells (SAEC) were pre-incubated with compound for 1 hour prior to stimulation with IL-13 for 15 minutes and phosphorylation of Stat6 was measured by intracellular flow cytometry.

Materials

Small Airway Epithelial Cells (SAEC) (LONZA, Cat# CC-2547)

Small Airway Epithelial Cell Growth Medium SAGM BulletKit™ (LONZA, Cat# CC-3118)

ReagentPack™ Subculture Reagents (LONZA, Cat# CC-5034)

Dimethyl Sulfoxide (DMSO) (Sigma-Aldrich, Cat# D2650)

Human IL-13 (Peprotech, Cat#200-13)

Human IL-4 (Peprotech, Cat# AF-200-04)

3.2% para-Formaldehyde (VWR, Cat# AA43368-9M)

Anti-Phospho Stat-6-AlexaFluor488 (pY641) (BD bioscience, Cat#558243)

FACS buffer: PBS+2% FBS (4° C.)

Method

SAEC were seeded at $2 \times 10^5$ cells/100 µl/well in a flat bottom 96-well plate. Compound was serially diluted in DMSO from 5 mM in 3-fold dilutions, and then diluted 3:125 in SAGM. 10 µL of 12× compound was added to the cells per well in duplicate and were preincubated for 1 hour at 37° C., 5% $CO_2$. Cells were then stimulated with 10 µL 12× IL-13 (10 ng/mL final) for 15 minutes at 37° C., 5% $CO_2$. The media was removed and the cells were briefly trypsinized, the trypsin neutralized with media, and the cells transferred to a round-bottom plate and washed in PBS. The cells were fixed by addition of 100 µL 3.2% paraformaldehyde in PBS for 15 minutes at room temperature. The cells were spun down for 5 minutes at 1000 rpm and the supernatant was discarded. The cells were permeabilized in 200 µL ice-cold methanol for 30 minutes at 4° C. then washed once with 200 µL of FACS buffer. Phospho-Stat6 was detected by staining the cells with 50 µL of AlexaFluor488-labeled anti-phospho-Stat6 antibody, diluted 1:100 in FACS buffer. Staining was carried out overnight at room temperature in the dark. The cells were washed in FACS buffer and the level of Stat6 phosphorylation was determined by FACS.

Example 2

Assay for Human Primary T-Cell Proliferation Stimulated by IL-2

Primary human T-cells derived from peripheral blood and pre-activated through stimulation of the T-cell receptor and CD28, proliferate in vitro in response to the cytokine Interleukin-2 (IL-2). This proliferative response is dependent on the activation of JAK-1 and JAK-3 tyrosine kinases, which phosphorylate and activate the transcription factor Stat-5.

Human primary T-cells were prepared as follows. Whole blood was obtained from a healthy volunteer, mixed 1:1 with PBS, layered on to Ficoll Hypaque (Amersham Pharmacia Biotech, Piscataway, N.J., Catalog #17-1440-03) in 2:1 blood/PBS:ficoll ratio and centrifuged for 30 min at 4° C. at 1750 rpm. The lymphocytes at the serum: ficoll interface were recovered and washed twice with 5 volumes of PBS. The cells were resuspended in Yssel's medium (Gemini Bio-products, Woodland, Calif., Catalog #400-103) containing 40 U/mL recombinant IL2 (R and D Systems, Minneapolis, Minn., Catalog #202-IL (20 µg)) and seeded into a flask pre-coated with 1 µg/mL anti-CD3 (BD Pharmingen, San Diego, Calif., Catalog #555336) and g/mL anti-CD28 (Immunotech, Beckman Coulter of Brea Calif., Catalog #IM1376). The primary T-cells were stimulated for 3-4 days, then transferred to a fresh flask and maintained in RPMI with 10% FBS and 40 U/mL IL-2.

The day prior to the assay set up, primary T-cells were centrifuged and resuspended in fresh RPMI with 10% FBS but without IL-2 and starved overnight. For the assay, the primary T-cells were centrifuged and resuspended Yssel's medium at $2 \times 10^6$ cells/mL. 50 µL of cell suspension containing 80 U/mL IL-2 was added to each well of a flat bottom 96 well black plate. For the unstimulated control, IL-2 was omitted from the last column on the plate. Compounds were serially diluted in dimethyl sulfoxide (DMSO, 99.7% pure, cell culture tested, Sigma-Aldrich, St. Louis, Mo., Catalog No. D2650) from 5 mM in 3-fold dilutions, and then diluted 1:250 in Yssel's medium. 50 µL of 2× compound was added per well in duplicate and the cells were allowed to proliferate for 72 hours at 37° C.

Proliferation was measured using CellTiter-Glo® Luminescent Cell Viability Assay (Promega), which determines the number of viable cells in culture based on quantitation of the ATP present, as an indicator of metabolically active cells. The substrate was thawed and allowed to come to ambient temperature. After mixing the Cell Titer-Glo reagent and diluent together, 100 µL was added to each well. The plates were mixed on an orbital shaker for two minutes to induce lysis and incubated at ambient temperature for an additional ten minutes to allow the signal to equilibrate. Detection was performed using a Wallac Victor2 1420 multilabel counter purchased from Perkin Elmer, Shelton, Conn.

The effectiveness of compounds A1-A18 to inhibit JAK3 activity, when tested under the conditions described above, are shown in Table 2 below. In Table 2, the activity is indicated by the following ranges: "A" represents compounds having an $IC_{50} < 0.5$ µM; "B" represents compounds having an $IC_{50} \geq 0.5$ M and $<5$ µM; and "--" represents no data available.

TABLE 2

| Compound | Activity |
|---|---|
| A1 | A |
| A2 | A |
| A3 | A |
| A4 | — |
| A5 | A |
| A6 | A |
| A7 | A |
| A8 | A |
| A9 | — |
| A10 | A |
| A11 | A |
| A12 | A |
| A13 | A |
| A14 | A |
| A15 | B |
| A16 | B |
| A17 | B |
| A18 | B |
| I-432 | A |

Example 3

Methods of Treatment

A subject in need of treatment for an inflammatory bowel disease is selected based on a clinical, diagnostic, and/or histopathological presentation of inflammatory bowel disease. For example, the subject may have symptoms of inflammatory bowel disease, such as abdominal pain, abdominal cramps, bloody diarrhea, vomiting, pelvic muscle spasms, and/or fever. Inflammatory bowel disease also may be determined by diagnostic tests and/or procedures, such as blood tests (e.g., to check for infection or antibodies characteristic of an inflammatory bowel disease), stool analysis, colonoscopy, flexible sigmoidoscopy, barium enema, abdominal x-ray, computerized tomography scan, magnetic resonance imaging, capsule endoscopy, and/or double-balloon endoscopy. Subjects also may be selected based on an increased risk of developing inflammatory bowel disease, such as a family history of inflammatory bowel disease and/or one or more genetic markers indicating a predisposition toward developing an inflammatory bowel disease.

The subject is administered a therapeutically effective dose of one or more of the compounds disclosed herein, or a pharmaceutical composition comprising one or more of the disclosed compounds. Administration may be performed via any suitable route including, but not limited to, parenteral (e.g., intravenous, intraperitoneal, implant), oral, or rectal routes. Treatment may be continued for at least a week, month, or year, and in some subjects treatment may extend over multiple years, the duration of disease, or the lifetime of the subject. Beneficial or desired results of treatment can include one or more, but are not limited to, alleviation or amelioration of one or more symptoms, diminishment of extent of the inflammatory bowel disease, stabilized (i.e., not worsening) state of the subject's condition, delay or slowing of the condition, including disease progression, amelioration or palliation of the condition, and remission (whether partial or total), whether detectable or undetectable.

In particular cases, subjects are selected for concomitant treatment with other pharmaceutical or non-pharmaceutical interventions, such as an analgesic, an antibiotic, an anticoagulant, an antibody, an anti-inflammatory agent, an immunosuppressant, or a combination thereof. In other cases, at least one embodiment of the disclosed compounds, or a pharmaceutical composition comprising the compound, is administered to the subject with no other treatment for the inflammatory bowel disease.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of treating or preventing alopecia in a subject in need thereof comprising topically administering to the subject a therapeutically effective amount of a compound selected from

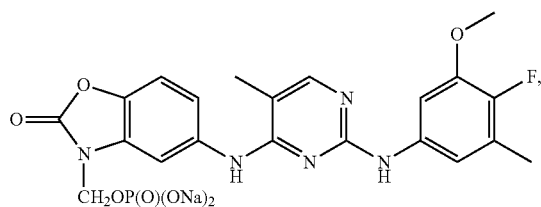

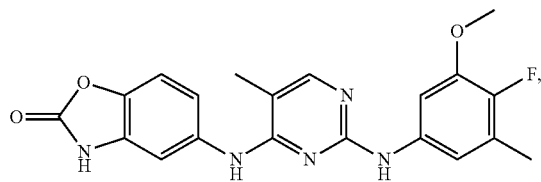 [SMILES: COc1cc(Nc2ncc(C)c(Nc3ccc4oc(=O)[nH]c4c3)n2)cc(C)c1F]

a hydrate thereof, a solvate thereof, an N-oxide thereof, a salt thereof, or a combination thereof.

2. The method of claim 1, wherein the compound is in a pharmaceutical composition further comprising a pharmaceutical acceptable carrier, diluent, excipient, preservative, stabilizer, or mixture thereof.

3. The method of claim 2, wherein the pharmaceutical composition is a solution, gel, ointment, cream, suspension, patch, adhesive disc, aerosol, or a combination thereof.

4. The method of claim 2, wherein the pharmaceutical composition is a topical solution.

5. The method of claim 1, wherein the subject has been identified as having alopecia or at a risk of developing alopecia.

6. The method of claim 1, wherein the compound is administered prophylactically to prevent or delay the onset of alopecia.

7. The method of claim 1, wherein the compound is

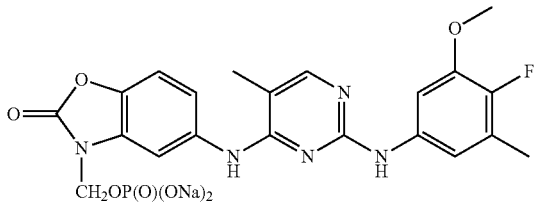

(Sodium (5-(2-(4-fluoro-3-methoxy-5-methylphenylamino)-5-methylpyriniidin-4-ylamino)-2-oxobenzo[d]oxazol-3 (2H)-yl)methyl phosphate).

8. The method of claim 1, wherein the compound is

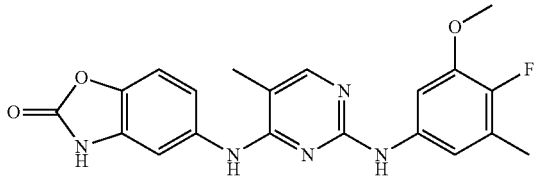 [SMILES: COc1cc(Nc2ncc(C)c(Nc3ccc4oc(=O)[nH]c4c3)n2)cc(C)c1F]

(5-(2-(4-fluoro-3-methoxy-5-methylphenylamino)-5-methylpyrimidin-4-ylamino)benzo[d]oxazol-2(3H)-one).

9. The method of claim 1, wherein the compound is a salt of

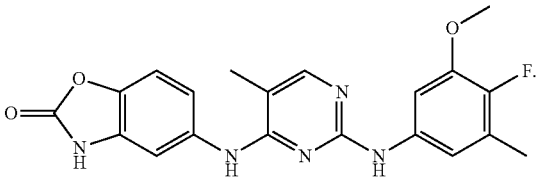 [SMILES: COc1cc(Nc2ncc(C)c(Nc3ccc4oc(=O)[nH]c4c3)n2)cc(C)c1F]

10. The method of claim 9, wherein the salt is selected from the group consisting of sodium, potassium, calcium, magnesium, ammonium, tetraalkylammonium, hydrochloride, hydrobromide, tartrate, mesylate, acetate, maleate, oxalate, sulfuric acid, nitrate, phosphoric acid, acetate, trifluoroacetate, propionate, glycolate, pyruvate, malonic acid, succinic acid, fumerate, citrate, benzoate, cinnamic acid, mandelic acid, methanesulfonic acid, ethanesulfonic acid, p-toluenesulfonic acid, salicylic acid, lithium, iron, zinc, copper, manganese, aluminum, salts of primary, secondary, and tertiary amines, salts of substituted amines, salts of cyclic amines, isopropylamine, trimethylamine, iethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, diethylamine, xinafoate salt, and a mixture thereof.

11. The method of claim 9, wherein the salt is a hydrochloride salt.

12. The method of claim 9, wherein the salt is a trifluoroacetate salt.

13. The method of claim 1, wherein the compound has a particle size of about 0.4 µm to about 5 µm.

14. The method of claim 1, wherein the compound has a particle size of less than about 5 µm.

15. The method of claim 1, wherein the therapeutically effective amount is a daily dose of about 1 mg/day to about 2 grams/day.

16. The method of claim 1, wherein the therapeutically effective amount is about 0.0001 mg/kg/day to about 100 mg/kg/day.

17. A method of treating or preventing alopecia in a subject in need thereof comprising orally administering to the subject a therapeutically effective amount of a compound selected from

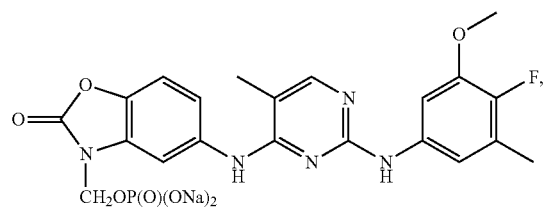

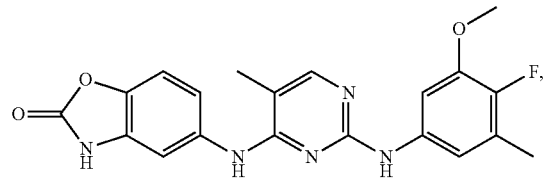

a hydrate thereof, a solvate thereof, an N-oxide thereof, a salt thereof, or a combination thereof.

18. The method of claim 17, wherein the compound is in a pharmaceutical composition further comprising a pharmaceutical acceptable carrier, diluent, excipient, preservative, stabilizer, or mixture thereof.

19. The method of claim 18, wherein the pharmaceutical composition in the form of lozenges, tablets, pills, capsules, troches, suspensions, dispersible powder, granules, emulsions, syrups, elixirs, enterocoated tablets, enterocoated pills, enterocoated capsules, or combinations thereof.

20. The method of claim 17, wherein the compound has a particle size of about 0.4 µm to about 5 µm.

21. The method of claim 17, wherein the compound has a particle size of less than about 5 µm.

22. The method of claim 17, wherein the compound is administered using a liposome delivery system.

23. The method of claim 17, wherein the compound is administered using an emulsion delivery system.

24. The method of claim 17, wherein the therapeutically effective amount is a daily dose of about 1 mg/day to about 2 grams/day.

25. The method of claim 17, wherein the therapeutically effective amount is about 0.0001 mg/kg/day to about 100 mg/kg/day.

26. The method of claim 17, wherein the compound is

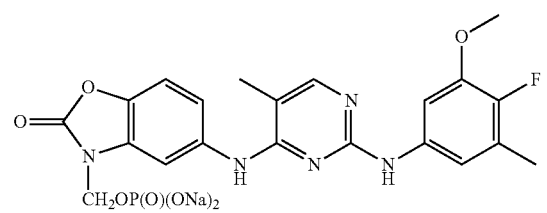

(Sodium (5-(2-(4-fluoro-3-methoxy-5-methylphenylamino)-5-methylpyriniidin-4-ylamino)-2-oxobenzo[d]oxazol-3 (2H)-yl)methyl phosphate).

27. The method of claim 17, wherein the compound is

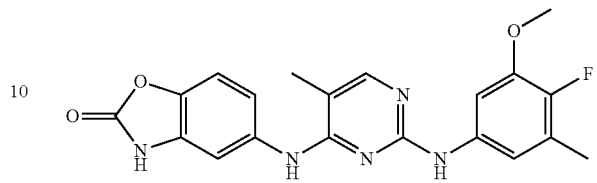

(5-(2-(4-fluoro-3-methoxy-5-methylphenylamino)-5-methylpyrimidin-4-ylamino)benzo[d]oxazol-2(3H)-one).

28. The method of claim 17, wherein the compound is a salt of

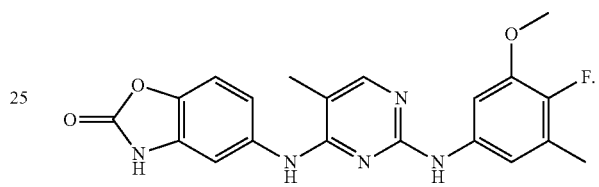

29. The method of claim 28, wherein the salt is selected from the group consisting of sodium, potassium, calcium, magnesium, ammonium, tetraalkylammonium, hydrochloride, hydrobromide, tartrate, mesylate, acetate, maleate, oxalate, sulfuric acid, nitrate, phosphoric acid, acetate, trifluoroacetate, propionate, glycolate, pyruvate, malonic acid, succinic acid, fumerate, citrate, benzoate, cinnamic acid, mandelic acid, methanesulfonic acid, ethanesulfonic acid, p-toluenesulfonic acid, salicylic acid, lithium, iron, zinc, copper, manganese, aluminum, salts of primary, secondary, and tertiary amines, salts of substituted amines, salts of cyclic amines, isopropylamine, trimethylamine, iethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, diethylamine, xinafoate salt, and a mixture thereof.

30. The method of claim 28, wherein the salt is a hydrochloride salt.

31. The method of claim 28, wherein the salt is a trifluoroacetate salt.

32. The method of claim 17, wherein the subject has been identified as having alopecia or at a risk of developing alopecia.

33. The method of claim 17, wherein the compound is administered prophylactically to prevent or delay the onset of alopecia.

* * * * *